United States Patent [19]

Chen et al.

[11] Patent Number: 5,581,350
[45] Date of Patent: Dec. 3, 1996

[54] METHOD AND SYSTEM FOR CALIBRATING AN ELLIPSOMETER

[75] Inventors: Xing Chen, San Jose; Philip D. Flanner, III, Union City; Kiron B. Malwankar, Sunnyvale; Jennming Chen, Campbell, all of Calif.

[73] Assignee: Tencor Instruments, Santa Clara, Calif.

[21] Appl. No.: 471,997

[22] Filed: Jun. 6, 1995

[51] Int. Cl.⁶ ..................................................... G01J 4/00
[52] U.S. Cl. ................................................................ 356/369
[58] Field of Search .................................... 356/369, 364; 250/225

[56] References Cited

U.S. PATENT DOCUMENTS

| | | | |
|---|---|---|---|
| 4,653,924 | 3/1987 | Itonaga et al. | 356/369 |
| 4,790,659 | 12/1988 | Erman et al. | 356/369 |
| 4,834,539 | 5/1989 | Le Bris et al. | 356/369 |
| 5,166,752 | 11/1992 | Spanier et al. | 356/369 |
| 5,329,357 | 7/1994 | Bernoux et al. | 356/369 |

OTHER PUBLICATIONS

Aspnes, et al., "High Precision Scanning Ellipsometer," Applied Optics, vol. 14, No. 1, pp. 220–228 (1975).
Bernoux, et al., "Ellipsometrie," Techniques de l'Ingenieur, R6490, pp. 1–16 (1990) (the original French text, and an English translation are attached).

*Primary Examiner*—Richard A. Rosenberger
*Assistant Examiner*—Amanda Merlino
*Attorney, Agent, or Firm*—Limbach & Limbach L.L.P.

[57] ABSTRACT

A method for calibrating an ellipsometer, and an ellipsometer including a processor programmed to control the analyzer, polarizer, and other ellipsometer components, and to process the data measured by the ellipsometer to perform the calibration method automatically. Where the ellipsometer's polarizer rotates and the analyzer remains fixed during measurement, the method determines coarse approximations of values $A_0$ and $P_0$, and then processes reflectivity data obtained at two or more analyzer angles to determine refined approximations of the values $A_0$ and $P_0$, where $P_0$ is the angle of the polarizer's optical axis at an initial time, and $A_0$ is the offset of the actual orientation angle of the analyzer from a nominal analyzer angle. Preferably the ellipsometer is a spectroscopic ellipsometer, the reflectivity data determine a $\tan\psi$ spectrum and a $\cos\Delta$ spectrum for each of the analyzer angles, and the coarse approximations of $A_0$ and $P_0$ are refined by processing the reflectivity data by performing regression on $A_0$ and $P_0$ until the differences among the $\tan\psi$ and $\cos\Delta$ spectra for several analyzer angles are minimized. Where the ellipsometer's analyzer rotates and the polarizer remains fixed during measurement, the method coarsely determines values $A'_0$ and $P'_0$, and then processes reflectivity data obtained at two or more polarizer angles to determine refined approximations of the values $A'_0$ and $P'_0$, where $P'_0$ is the angle of the analyzer's optical axis at an initial time, and $A'_0$ is the offset of the actual orientation angle of the polarizer from a nominal polarizer angle.

20 Claims, 6 Drawing Sheets

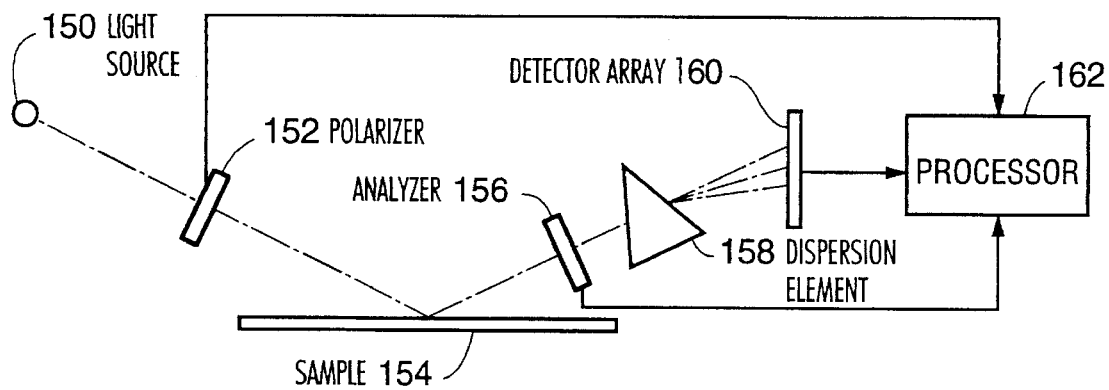
FIG. 1
(PRIOR ART)
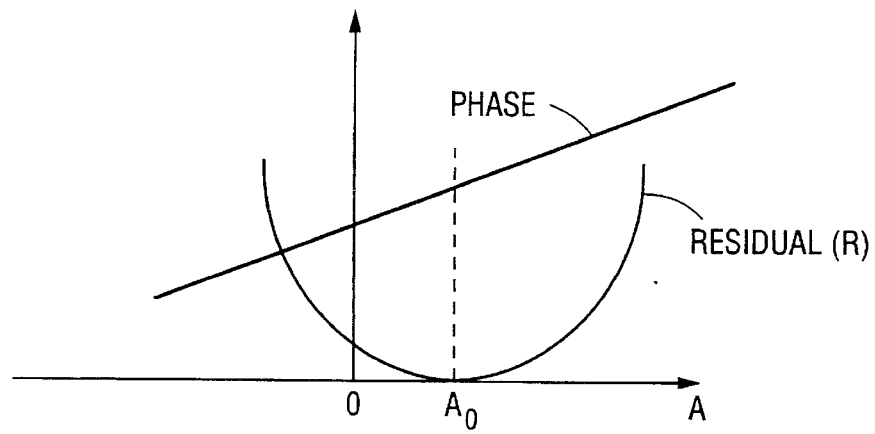
FIG. 2
(PRIOR ART)
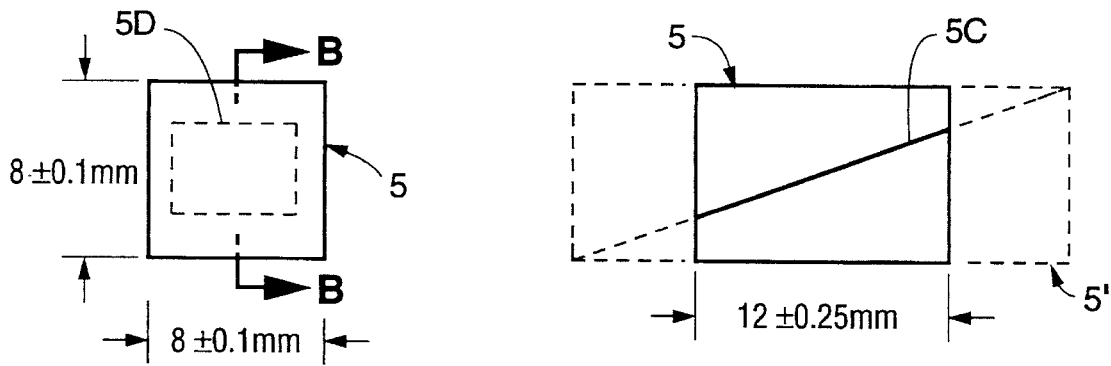
FIG. 5  FIG. 6

METHOD AND SYSTEM FOR CALIBRATING AN ELLIPSOMETER

FIELD OF THE INVENTION

The invention relates to a method for calibrating an ellipsometer (such as a spectroscopic ellipsometer), and to an ellipsometer (such as a spectroscopic ellipsometer) including a means for automatically performing such calibration method.

BACKGROUND OF THE INVENTION

Among the well known nondestructive testing techniques is the technique of spectroscopic ellipsometry, which measures reflectance data by reflecting electromagnetic radiation from a sample (typically to measure the thickness of a very thin film on a substrate). In spectroscopic ellipsometry, an incident radiation beam having a known polarization state reflects from a sample, and the polarization of the reflected radiation is analyzed to determine properties of the sample. Since the incident radiation includes multiple frequency components, a spectrum of measured data (including data for incident radiation of each of at least two frequencies) can be measured. Typically, the polarization of the incident beam has a time-varying characteristic (produced, for example, by passing the incident beam through a mechanically rotating polarizer), and/or the means for analyzing the reflected radiation has a time-varying characteristic (for example, it may include a mechanically rotating analyzer). Examples of spectroscopic ellipsometry systems are described in U.S. Pat. No. 5,329,357, issued Jul. 12, 1994 to Bernoux, et al., and U.S. Pat. No. 5,166,752, issued Nov. 24, 1992 to Spanier, et al. Spectroscopic ellipsometry theory is described in F. Bernoux, et al., "Ellipsometrie," Techniques de l'Ingenieur, R6490, pp. 1–16 (1990).

Reflectance data (measured by spectroscopic ellipsometry or other reflection techniques) are useful for a variety of industrial applications. The thickness of various coatings (either single layer or multiple layer) on a substrate can be determined from spectroscopic ellipsometry data (indicative of the polarization of radiation reflected from the sample in response to incident radiation having known polarization state), or a reflectance spectrum or relative reflectance spectrum.

The reflectance of a sample (or sample layer) at a single wavelength can be determined by analyzing spectroscopic ellipsometry data (indicative of the polarization changes of radiation reflected from the sample, in response to incident radiation having known polarization state) or extracted from an accurately measured reflectance or relative reflectance spectrum. It is useful to determine sample reflectance in this way where the reflectance of photoresist coated wafers at the wavelength of a lithographic exposure tool must be found, to determine proper exposure levels for the wafers or to optimize the thickness of the resist to minimize reflectance of the entire coating stack.

The present invention pertains to calibration of an ellipsometer (such as a spectroscopic ellipsometer). To appreciate the difference between the inventive calibration method, and conventional calibration methods, it is helpful to consider the method of operation of a spectroscopic ellipsometer.

FIG. 1 is a schematic diagram of a typical spectroscopic ellipsometer. In operation of this ellipsometer, a beam of broadband radiation from broadband radiation source 150 is linearly polarized in polarizer 152, and the linearly polarized beam is then incident on sample 154o After reflection from sample 154, the beam propagates toward analyzer 156 with a changed polarization state (typically, the reflected beam has elliptical polarization, where the polarized beam emerging from polarizer 152 had linear polarization). The reflected beam propagates through analyzer 156 into dispersion element (spectrometer) 158. In dispersion element 158, the beam components having different wavelengths are refracted in different directions to different detectors of detector array 160. Processor 162 receives the measured data from each detector of array 160, and is programmed with software for processing the data it receives in an appropriate manner. Detector array 160 can be a linear array of photodiodes, with each photodiode measuring radiation in a different wavelength range.

Either polarizer 152 or analyzer 156 is rotatably mounted for rotation about the optical axis during a measurement operation (or both of them are so rotatably mounted). During a typical measurement operation, polarizer 152 is rotated and analyzer 156 remains in a fixed orientation, or analyzer 156 is rotated and polarizer 152 remains fixed.

Processor 162 can be programmed to generate control signals for controlling the rotation (or angular orientation) of polarizer 152 and/or analyzer 156, or for controlling other operating parameters of elements of the FIG. 1 system (such as the position of a movable sample stage on which sample 154 rests). Processor 162 can also receive data (indicative of the angular orientation of analyzer 156) from an analyzer position sensor associated with analyzer 156 and data (indicative of the angular orientation of polarizer 152) from a polarizer position sensor associated with polarizer 152, and can be programmed with software for processing such orientation data in an appropriate manner.

If polarizer 152 is controlled so that it rotates at a constant speed, the signal received at each detector of array 160 will be a time-varying intensity given by:

$$I(t) = I_0[1 + \alpha \cos(2\omega t - P_0) + \beta \sin(2\omega t - P_0)] \quad (1)$$
$$= I_0[1 + \alpha'\cos(2\omega t) + \beta' \sin(2\omega t)]$$

where $I_0$ is a constant that depends on the intensity of radiation emitted by source 150, $\omega$ is the angular velocity of polarizer 152, $P_0$ is the angle between the optical axis of polarizer 152 and the plane of incidence (e.g., the plane of FIG. 1) at an initial time (t=0), and $\alpha$ and $\beta$ are sample related values defined as follows:

$$\alpha = [\tan^2\psi - \tan^2(A-A_0)]/[\tan^2\psi + \tan^2(A-A_0)] \quad (2)$$

and $$\beta = 2(\tan\psi)(\cos\Delta)(\tan(A-A_0)/[\tan^2\psi + \tan^2(A-A_0)] \quad (3)$$

where $\tan\psi$ is the amplitude of the complex ratio of the p and s components of the reflectivity of the sample, $\Delta$ is the phase of the complex ratio of the p and s components of the reflectivity of the sample (where "p" denotes the component for polarized radiation whose electrical field is in the plane of FIG. 1, and "s" denotes the component for polarized radiation whose electrical field is perpendicular to the plane of FIG. 1), A is the nominal analyzer angle (a reading of analyzer 156's orientation angle, supplied for example from the above-mentioned analyzer position sensor associated with analyzer 156), and $A_0$ is the offset of the actual orientation angle of analyzer 156 from the reading "A" (due to mechanical misalignment, $A_0$ can be non-zero).

The values $\alpha'$ and $\beta'$ are also sample related values, defined as follows:

$$\alpha'=\alpha\cos(2P_0)+\beta\sin(2P_0) \quad (4)$$

and $$\beta'=\alpha\sin(2P_0)-\beta\cos(2P_0) \quad (5)$$

where $\alpha$, $\beta$, and $P_0$ are defined above.

To achieve measurement accuracy, it is crucial to determine $P_0$ and $A_0$ very precisely.

Conventionally, $P_0$ and $A_0$ are calibrated simultaneously by a method known as the "minimum residual method," first proposed in David E. Aspnes and A. A. Studna, "High Precision Scanning Ellipsometer," Applied Optics, Vol. 14, No. 1, pp. 220–228 (1975). The minimum residual method is still widely used by ellipsometer users and manufacturers as of the filing date of this specification.

The conventional minimum residual method determines (from measured data) a quantity known as the "residual" (R), which is:

$$R=1-\alpha^2-\beta^2 \quad (6)$$

where $\alpha$ and $\beta$ are defined in equations (2) and (3).

An equivalent quantity is $R'=1-\alpha'^2-\beta'^2$ where $\alpha'$ and $\beta'$ are defined in equations (4) and (5). Of course, it follows from equations (2) through (5) that $R=R'$, and both $R$ and $R'$ are denoted herein as the "residual."

Using equations (2) and (3), it is apparent that the residual, $R$, can also be expressed as:

$$R=(4-\cos^2\Delta)\tan^2\psi\tan^2(A-A_0)/[\tan^2\psi+\tan^2(A-A_0)]^2 \quad (7)$$

By orienting the analyzer so that $A-A_0=\delta A$ is very small, it can be assumed that $\tan\delta A$ is approximately equal to $\delta A$. Under this condition, equation (7) can be approximated by:

$$R=(4-\cos^2\Delta)(\delta A/\tan\psi)^2[1-2(\delta A/\tan\psi)^2] \quad (8)$$

The "phase" of the residual $R$ is defined by:

$$\begin{aligned}\text{Phase} &= \tan^{-1}(\beta'/\alpha') \quad (9)\\ &= \tan^{-1}[\alpha\sin(2P_0)-\beta\cos(2P_0)/(\alpha\cos(2P_0)+\beta\sin(2P_0))]\end{aligned}$$

where $\alpha'$ and $\beta'$ are defined by equations (4) and (5).

To perform calibration (i.e., determine the values $A_0$ and $P_0$) in accordance with the conventional minimum residual method, the orientation of analyzer 156 is first scanned around the zero position, the values R and "Phase" are determined from the measured data at each measured value (A) of the analyzer's orientation, and the values R and "Phase" are plotted as a function of A, to generate a graph such as that shown in FIG. 2.

Then, the value $A_0$ (the offset between analyzer 156's actual orientation angle and each reading "A") is identified as the minimum of the "R v. A" curve. When $A=A_0$, it is true that $\alpha=1$ and $\beta=0$, so that Phase$=2P_0$. Thus, having identified the value $A_0$, the minimum residual method identifies $2P_0$ as the value of the "Phase v. A" curve at $A=A_0$.

To accurately determine the minimum of the "R v. A" curve, it is necessary to fit the bottom part of this curve with a parabolic curve. However, this cannot be done accurately under all conditions, for the reasons explained with reference to FIG. 3.

FIG. 3 is a graph of three "R v. A" curves, each generated from measurements at $\cos(\Delta)=1$ a different value of $\tan(\psi)$, namely $\tan(\psi)=10$, $\tan(\psi)=0.1$ and $\tan(\psi)=1$. From FIG. 3, it is apparent that the shape of the "R v, A" curve strongly depends on the value of $\tan(\psi)$. If $\tan(\psi)$ is too small or too large, the bottom part of the curve is very flat, in which case a small perturbation caused by noise can cause a large shift in the estimated value of the curve's minimum position. Thus, the conventional "minimum residual method" is reliable and accurate only for samples for which the value of $\tan(\psi)$ is in a very limited range.

There are several other important limitations of prior art calibration methods (including the "minimum residual method"), including that they can be performed accurately only on very thick samples. Until the present invention, it had not been known how to avoid these limitations of prior art calibration methods.

SUMMARY OF THE INVENTION

The inventive method for calibrating an ellipsometer includes the steps of determining coarse approximations of the above-defined values $A_0$ and $P_0$; and then processing reflectivity data obtained at two or more analyzer angles to determine refined approximations of the values $A_0$ and $P_0$. Where the ellipsometer is a spectroscopic ellipsometer, the reflectivity data determine a $\tan\psi$ spectrum and a $\cos\Delta$ spectrum for each analyzer angle, each set of reflectivity data measured by operating the ellipsometer (with a rotating polarizer) at a different analyzer angle. The $\tan\psi$ and $\cos\Delta$ spectra for each analyzer angle determine the amplitude and phase of the complex ratio of p and s components of sample reflectivity (at each of at least two incident radiation frequencies). Where the ellipsometer is not a spectroscopic ellipsometer, the reflectivity data determine a $\tan\psi$ value and a $\cos\Delta$ value (for only single frequency or frequency range of incident radiation) for each analyzer angle.

Preferably, the coarse approximations of $A_0$ and $P_0$ are refined by processing the reflectivity data in the following manner. The reflectivity data are processed to determine $\tan\psi$ and $\cos\Delta$ values (e.g., $\tan\psi$ and $\cos\Delta$ spectra) and regression is performed on $A_0$ and $P_0$ until the differences among the determined $\tan\psi$ and $\cos\Delta$ values for the different analyzer angles are minimized. In a class of preferred embodiments, the regression is performed using the well-known least square fit algorithm or another function minimization technique.

Preferably, the invention generates data determining the coarse approximation of $A_0$ as follows. A first nominal residual value is acquired with the fixed analyzer at a first nominal analyzer angle $A_1$. Then, nominal residual values are acquired at several nominal analyzer angles $A_i$ all approximately equal to $-A_1$, and a second nominal analyzer angle ($A_2$) is identified, where $-A_2$ is the one of the several nominal angles at which the nominal residual value is closest to the first nominal residual value. By averaging the first and second nominal analyzer angles, the coarse approximation of $A_0$ is determined.

Preferred embodiments of the inventive ellipsometer include a processor programmed to generate control signals for controlling the analyzer, polarizer, and other components of the ellipsometer appropriately, and to perform appropriate processing of the measured data received from the detector (or each detector of the detector array) of the ellipsometer, to perform the inventive calibration method automatically.

Alternative embodiments of the invention are a method for calibrating an ellipsometer (where the ellipsometer has an analyzer that rotates during measurement of a sample and a fixedly mounted polarizer), and an ellipsometer of this type including a means for performing such method automatically. These embodiments implement a modified version of the above-described calibration method which determines coarse approximations (and then refined approximations) of values $P'_0$ and $A'_0$, where $A'_0$ is the angle (at an initial time, t=0) of the analyzer optical axis, and $P'_0$ is the offset of the actual orientation angle of the fixed polarizer from a nominal angle P' of the fixed polarizer.

BRIEF DESCRIPTION OF THE DRAWINGS

FIG. 1 is a schematic diagram of a spectroscopic ellipsometer which can be calibrated in accordance with the method of the invention.

FIG. 2 is a graph of residual (R) versus analyzer angle (A), and phase of the residual "Phase") versus analyzer angle (A), of a type generated during a conventional spectroscopic ellipsometer calibration method.

FIG. 5 is a simplified cross-sectional view (taken along line A—A of FIG. 4) of a preferred embodiment of polarizer 5 of FIG. 4.

FIG. 6 is a simplified cross-sectional view (taken along line B—B of FIG. 5) of the FIG. 5 embodiment of polarizer 5 (showing, for purposes of comparison, a conventional polarizer 5' in phantom view).

DESCRIPTION OF THE PREFERRED EMBODIMENTS

Throughout the specification, the phrase "incidence angle" of radiation at a surface denotes the angle between the normal to the surface and the propagation direction of the radiation. Thus, radiation with normal incidence at a sample surface has an incidence angle of zero degrees, and radiation with grazing incidence at such surface has an incidence angle substantially equal to 90°. Throughout the specification, the phrase "high incidence angle" denotes an incidence angle greater than 30°.

Throughout the specification, the phrase "broadband radiation" denotes radiation whose frequency-amplitude spectrum includes two or more different frequency components. For example, broadband radiation may comprise a plurality of frequency components in the range from 230 nm to 850 nm.

Figure 3:
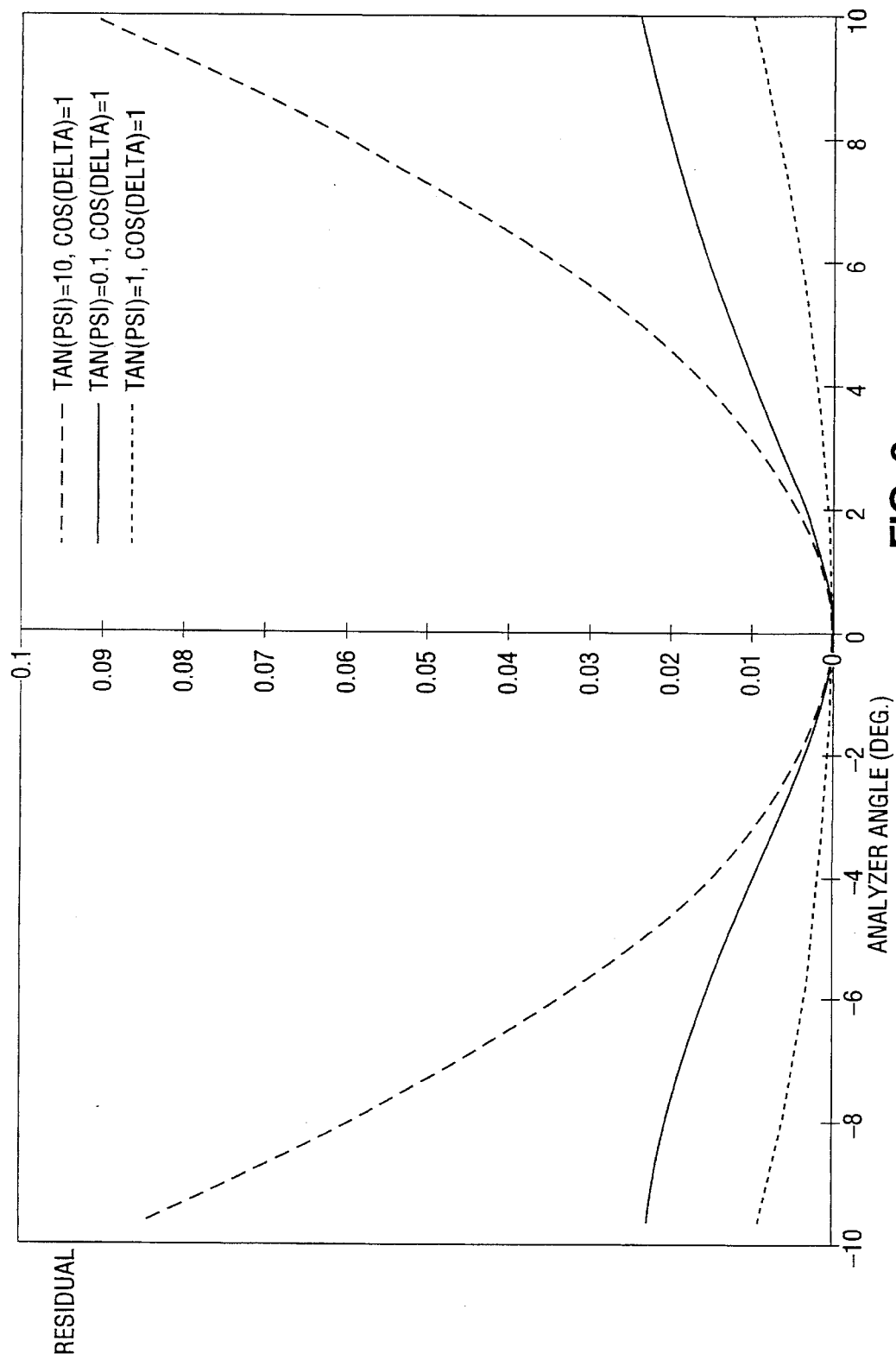
FIG. 3 is a graph of residual (R) versus analyzer angle (A), for each of three different value pairs $\tan(\psi)$ and $\cos(\Delta)$, as generated during a conventional spectroscopic ellipsometer calibration method.
Figure 4:
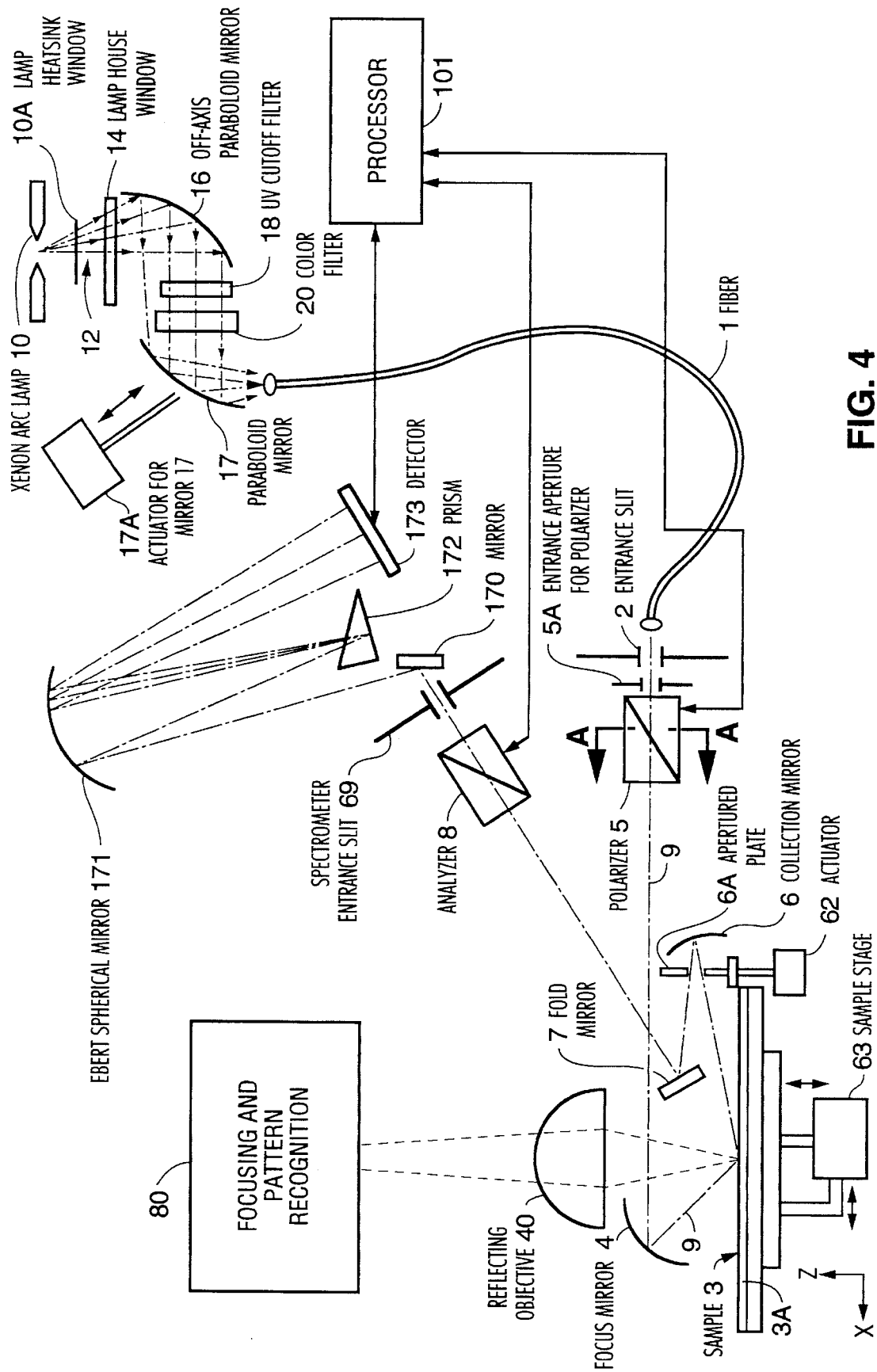
FIG. 4 is a schematic diagram of a preferred embodiment of a spectroscopic ellipsometer which is programmed to perform the method of the invention automatically. This ellipsometer includes processor 101 which is programmed to control analyzer 8 and polarizer 5 (and other components of the ellipsometer) appropriately, and to perform the appropriate processing of the measured data it receives from detector array 173, to perform the inventive calibration method automatically.

Throughout the specification, including in the claims, the term "software" is employed in a broad sense to denote code which programs (instructions which program) a general purpose data processing apparatus, or firmware (microcode which resides in a read-only-memory apparatus). For example, when processor 101 of FIG. 4 is said to be programmed with software for generating control signals for controlling the orientation of rotatably mounted analyzer 8, such software can be implemented as firmware in processor 101 (e.g., when processor 101 is not a general purpose computer, but is instead another data processing apparatus).

The inventive method for calibrating a spectroscopic ellipsometer has two steps: determining coarse approximations of the above-defined values $A_0$ and $P_0$; and then processing reflectivity data ($\tan\psi$ and $\cos\Delta$ spectra) obtained at two or more analyzer angles to determine refined approximations of the values $A_0$ and $P_0$. The reflectivity data determine a $\tan\psi$ spectrum and a $\cos\Delta$ spectrum for each of at least two analyzer angles, each set of reflectivity data measured by operating a spectroscopic ellipsometer (with a rotating polarizer) at a different analyzer angle. The $\tan\psi$ and $\cos\Delta$ spectra for each analyzer angle determine the amplitude and phase of the complex ratio of p and s components of sample reflectivity (at each of at least two incident radiation frequencies).

Preferably, the coarse approximations of $A_0$ and $P_0$ are refined by processing the reflectivity data in the following manner. Regression is performed on $A_0$ and $P_0$ (preferably using the well-known least square fit algorithm or another function minimization technique), until the differences among the $\tan\psi$ and $\cos\Delta$ spectra for several analyzer angles are minimized. More specifically, to implement such regression, a $\tan\psi$ spectrum and a $\cos\Delta$ spectrum for each of the analyzer angles is computed from the reflectivity data using the coarse approximations of $A_0$ and $P_0$. Then, regression is performed on $A_0$ and $P_0$ to generate a revised $\tan\psi$ spectrum and a revised $\cos\Delta$ spectrum (for each of the analyzer angles) for each of a number of different value pairs $A_0$ and $P_0$, and computing (for each of the value pairs $A_0$ and $P_0$) the differences between the revised $\tan\psi$ and $\cos\Delta$ spectra for pairs of the analyzer angles, until such differences are minimized. The invention identifies as the refined approximations of $A_0$ and $P_0$ those values of $A_0$ and $P_0$ which result in minimization of such differences.

The invention is based on recognition that when an ellipsometer (with rotating polarizer and fixed analyzer) is used to measure reflectivity data (e.g., when a spectroscopic ellipsometer with rotating polarizer and fixed analyzer is used to measure reflectivity data determining $\tan\psi$ and $\cos\Delta$ spectra), the $\tan\psi$ and $\cos\Delta$ spectra are independent of the analyzer angle. The invention is also based on recognition that this phenomenon can be exploited to estimate $A_0$ and $P_0$ in efficiently and accurately for virtually any sample.

We next describe preferred embodiments of the calibration method of the invention which determine (from measured data obtained by operating a spectroscopic ellipsometer or other ellipsometer) the same "residual" value defined above in equation (6), namely $R=1-\alpha^2-\beta^2=1-\alpha'^2-\beta'^2=R'$.

When the ellipsometer is operated (to measure reflectivity data) with a rotating polarizer and fixed analyzer, the residual depends on the actual analyzer angle (a reading of the analyzer angle adjusted by the offset of the reading from the actual angle).

In calibrating an ellipsometer with a rotating polarizer and fixed analyzer, the method of the invention determines coarse approximations of $A_0$ and $P_0$ as follows. First, data determining a nominal residual value $R'(A_1)$ are acquired with the fixed analyzer at a first nominal analyzer angle $A_1$. This is done without knowledge of values $A_0$ and $P_0$ by assuming (for the purpose of determining the nominal residual value $R'(A_1)$) that $A_0=0$, and employing equation (7) to process data (indicative of $A_1$ and $\cos\Delta$ and $\tan\psi$ values for analyzer angle $A_1$) to generate data indicative of the value $R'(A_1)=(4-\cos^2\Delta)\tan^2\psi\tan^2(A_1)/[\tan^2\psi+\tan^2(A_1)]^2$.

Similarly, data determining nominal residual values $R'(A_i)$ are acquired at several nominal analyzer angles $A_i$, all approximately equal to $-A_1$.

Preferably, nominal angle $A_1$ is chosen so that $\tan(A_1) > \tan\psi$ for all wavelengths. This can be achieved easily by using a sample consisting of bare silicon or glass, and setting $A_1=45$ degrees. If $\tan(A_1)$ is less than or equal to $\tan\psi$ for at least one relevant wavelength, then the coarse approximation of $P_0$ (determined in the manner described below) can differ by 90 degrees from the correct value.

Then, the inventive method exploits the fact that the actual value $R'$ satisfies the symmetry relation $R'(A-A_0)=R'[-(A-A_0)]$, by determining a second nominal analyzer angle $A_2$ at which the nominal value $R'(-A_2)$ is closest to the nominal value $R'(A_1)$. The second nominal angle $A_2$, which has the same sign as the first nominal angle $A_1$, is equal to $A_2=-A_{i1}$, where $+A_{i1}$ is one of the nominal analyzer angles $A_i$ that are approximately equal to $-A_1$.

Then, the invention averages the two nominal angles $A_2$ and $A_1$, and identifies the resulting averaged value (shown in equation (10)) as the coarse approximation of $A_0$:

$$A_0 = (A_1 + A_2)/2 \qquad (10)$$

Using this coarse approximation of $A_0$, the invention determines the coarse approximation of $P_0$ as follows. In order readily to understand the preferred method for coarsely approximating $P_0$, it is helpful to employ equations (2) and (3) to define the following quantities:

$$\alpha_+ = \alpha(A-A_0) = \alpha[-(A-A_0)] = \alpha_- \qquad (11)$$

and $$\beta_+ = \beta(A-A_0) = -\beta[-(A-A_0)] = -\beta_- \qquad (12)$$

With the notation $\alpha'(A_1-A_0)=\alpha_+'$, $\alpha'[-(A_2-A_0)]=\alpha_-'$, $\beta'(A_1-A_0)=\beta_+'$, and $\beta'[-(A_2-A_0)]=\beta_-'$, and using equations (11), (12), (4), and (5), it is seen that:

$$\alpha_+' + \alpha_-' = 2\alpha\cos(2P_0) \qquad (13)$$

and $$\beta_+' + \beta_-' = 2\alpha\sin(2P_0) \qquad (14)$$

The invention thus determines the coarse approximation of $P_0$ to be:

$$P_0 = \tan^{-1}[(\beta_+'+\beta_-')/(\alpha_+'+\alpha_-')]/2 \qquad (15)$$

The values $\alpha'(A_1-A_0)=\alpha_+'$, $\alpha'[-(A_2-A_0)]=\alpha_-'$, $\beta'(A_1-A_0)=\beta_+'$, and $\beta'[-(A_2-A_0)]=\beta_-'$ in equation (15) are preferably determined (using the well known Hadamard algorithm) as follows, where each detector is a charge integrating detector (e.g., where array 173 is an intensified photodiode array). Using an array of such charge integrating detectors, the output of each detector is proportional to the charge it collects during a period, T, known as the integration time. The output of each detector is thus given by:

$$S = \int_0^T I(t)dt = \int_{P_0+P_s}^{P_0+P_e} I(P)dP$$

where $I(t)$ is defined above, T is the integration time, $P_s$ is the starting polarizer angular position, $P_e$ is the ending polarizer angular position, and $P=\omega t$. By dividing one polarizer revolution into eight segments and measuring (integrating) the signal $I(t)$ over each of those segments, we measure the following eight signals:

$$S_1 = \int_0^{\pi/4} I(P)dP = \frac{I_0}{2}\left(\frac{\pi}{2}+\alpha'+\beta'\right)$$

$$S_2 = \int_{\pi/4}^{\pi/2} I(P)dP = \frac{I_0}{2}\left(\frac{\pi}{2}-\alpha'+\beta'\right)$$

$$S_3 = \int_{\pi/2}^{3\pi/4} I(P)dP = \frac{I_0}{2}\left(\frac{\pi}{2}-\alpha'-\beta'\right)$$

$$S_4 = \int_{3\pi/4}^{\pi} I(P)dP = \frac{I_0}{2}\left(\frac{\pi}{2}+\alpha'-\beta'\right)$$

$$S_5 = \int_{\pi}^{5\pi/4} I(P)dP = \frac{I_0}{2}\left(\frac{\pi}{2}+\alpha'+\beta'\right) = S_1$$

$$S_6 = \int_{5\pi/4}^{3\pi/2} I(P)dP = \frac{I_0}{2}\left(\frac{\pi}{2}-\alpha'+\beta'\right) = S_2$$

$$S_7 = \int_{3\pi/2}^{7\pi/4} I(P)dP = \frac{I_0}{2}\left(\frac{\pi}{2}-\alpha'-\beta'\right) = S_3$$

$$S_8 = \int_{7\pi/4}^{2\pi} I(P)dP = \frac{I_0}{2}\left(\frac{\pi}{2}+\alpha'-\beta'\right) = S_4$$

Each of the eight signals $S_i$ is known as a "sum." By processing the sums (and using equation (2), we determine $\alpha'$ and $\beta'$ to be:

$$\alpha' = (1/4I_0)(S_1-S_2-S_3+S_4+S_5-S_6-S_7+S_8)$$

and $$\beta' = (1/4I_0)(S_1+S_2-S_3-S_4+S_5+S_6-S_7-S_8)$$

where $I_0 = (1/2\pi)(S_1+S_2+S_3+S_4+S_5+S_6+S_7+S_8)$.

By processing sums $(S_i)$ measured with the analyzer at a nominal angle A, the values $\alpha_+'$ and $\beta_+'$ are determined by the equations in the previous paragraph. Then, by processing sums $(S_i)$ measured with the analyzer at the opposite nominal angle $(-A)$, the values $\alpha_-'$ and $\beta_-'$ are determined by the equations in the previous paragraph. Having thus determined $\beta_+'$, $\beta_-'$, $\alpha_+'$, and $\alpha_-'$, equation (15) determines the coarse approximation of $P_0$.

If a photodetector array (such as a photodiode array or a linear CCD) is used to implement detector array 173, the coarse approximation of $P_0$ for each element of the array can be determined as follows. Typically, when the array is used to record reflectivity data at multiple wavelengths, each detector element is initiated at a different polarizer angle. Accordingly, $P_0$ is different for each element of the array. In most cases, $P_0$ for a particular one of the detector elements ($P_{ON}$) can be assumed to be a linear function of the element's position:

$$P_{ON} = aN + b,$$

where N is a non-negative integer identifying each of the elements (the "first" detector element is identified by N=0), "b" is $P_0$ for the first detector element, and "a" is a constant known as "$P_0$-slope". The $P_0$-slope (the value of "a") depends only on the integration time and readout time of the array, and hence can be precisely calculated.

Having determined coarse approximations of the values $A_0$ and $P_0$ (for each detector), the invention then determines refined approximations of the coarsely approximated values $A_0$ and $P_0$, in the following manner. First, the ellipsometer undergoing calibration is operated to measure reflectivity data at each of two or more analyzer angles (with a rotating polarizer and fixed analyzer at each of the analyzer angles). If the ellipsometer is a not a spectroscopic ellipsometer, the reflectivity data (for each analyzer angle) determine both a $\tan\psi$ value and a $\cos\Delta$ value for one incident radiation frequency (or frequency range).

If the ellipsometer being calibrated is a spectroscopic ellipsometer, the reflectivity data (for each analyzer angle) determine both a $\tan\psi$ value and a $\cos\Delta$ value for each of two or more incident radiation frequencies (or frequency ranges). In this case, the reflectivity data determine a $\tan\psi$ spectrum and a $\cos\Delta$ spectrum for each analyzer angle. The $\tan\psi$ and $\cos\Delta$ spectra for each analyzer angle determine the amplitude and phase of the complex ratio of p and s components of sample reflectivity (at each of two or more incident radiation frequencies).

For example, when calibrating the spectroscopic ellipsometer of FIG. 1, the reflectivity data (for each angle of analyzer 156) typically consist of a sequence of readings of detector array 160 taken while polarizer 152 rotates, with each read-out of detector array 160 initiated at a different angular position of polarizer 152 (and integrated over forty-five degrees of polarizer rotation).

In accordance with the invention, the reflectivity data (which determine $\tan\psi$ and $\cos\Delta$ values or $\tan\psi$ and $\cos\Delta$ spectra) obtained at the multiple analyzer angles are processed to determine refined approximations of the values $A_0$ and $P_0$. In preferred embodiments, this processing is accomplished by performing regression on $A_0$ and $P_0$ (preferably using the well-known least square fit algorithm) as follows. A $\tan\psi$ and $\cos\Delta$ value pair (or $\tan\psi$ spectrum and a $\cos\Delta$ spectrum) for each of the analyzer angles is computed from the reflectivity data using the coarse approximations of $A_0$ and $P_0$. Then, regression is performed on $A_0$ and $P_0$ to generate a revised $\tan\psi$ and $\cos\Delta$ value pair (or a revised $\tan\psi$ spectrum and a revised $\cos\Delta$ spectrum) for each of the analyzer angles (and for each of a number of different value pairs $A_0$ and $P_0$), and computing (for each of the value pairs $A_0$ and $P_0$) an error term for (e.g., differences between) revised $\tan\psi$ and $\cos\Delta$ values (or spectra) for different analyzer angles, until such error term is minimized. As a result of such regression, preferred embodiments of the invention identify the values of $A_0$ and $P_0$ which result in the minimum total difference between the $\tan\psi$ and $\cos\Delta$ values (or $\tan\psi$ and $\cos\Delta$ spectra) for each pair of analyzer angles, as the refined approximations of $A_0$ and $P_0$.

The first phase of the inventive method (determining coarse approximations of $A_0$ and $P_0$) is necessary to ensure that the regression operation (the second phase of the inventive method) converges rapidly to the correct values (refined approximations) of $A_0$ and $P_0$.

The regression step of the inventive method exploits the fact that when an ellipsometer is operated with a rotating polarizer and fixed analyzer to measure data which determine $\tan\psi$ and $\cos\Delta$ values (or a $\tan\psi$ spectrum and a $\cos\Delta$ spectrum), such values (or spectra) are independent of analyzer angle (for any given sample).

Next, we describe in greater detail a class of embodiments in which the regression step (for calibrating a spectroscopic ellipsometer with a fixed analyzer and rotating polarizer) is performed using a standard function minimization technique. In describing these embodiments, we assume that:

1. a set of n spectra have been measured, each at a different analyzer angle $A_n$ (where the absolute value of each angle $A_n$ is greater than 10 degrees);
2. the coarsely approximated value of $A_0$ is in the range [−10 degrees, +10 degrees];
3. "b" (the above-discussed coarsely approximated value of $P_0$ for the first detector element) is known to within plus or minus 10 degrees; and
4. "a" (the above-discussed "$P_0$-slope") is known to within plus or minus 0.02 degrees.

These assumptions ensure that the sign of the true value of each analyzer angle $A_n$ is known, and reduce the chance of multiple possible solutions for "b" and "a."

We use the notation $\cos\Delta_{ij}$ to denote the measured value of $\cos\Delta$ at frequency "i" and analyzer position $A_j$, and $\tan\psi_{ij}$ to denote the measured value of $\tan\psi$ at frequency "i" and analyzer position $A_j$. $\cos\Delta_{ij}$ is a function of "a," "b," the eight sums defined above ($S_1$ through $S_8$), and the sign of $A_j - A_0$. $\tan\psi_{ij}$ is a function of "a," "b," the raw signal $T_{kij}$, and $\tan(A_j - A_0)$.

Let $$\overline{\cos\Delta_i} = \frac{1}{n} \sum_{j=1}^{n} \cos\Delta_{ij}$$

be the mean value of $\cos\Delta_{ij}$ (over all analyzer positions) for a single frequency.

Let $$\overline{\tan\Psi_i} = \frac{1}{n} \sum_{j=1}^{n} \tan\Psi_{ij}$$

be the mean value of $\tan\psi_{ij}$ (over all analyzer positions) for a single frequency.

We define an error term to be one of $$E_{MSE} = \sum_i \sum_j \left[ \frac{\cos\Delta_{ij} - \overline{\cos\Delta_i}}{\delta\cos\Delta_{ij}} \right]^2$$

or $$E_{MINMAX} = \max_i \sum_j \left[ \frac{\cos\Delta_{ij} - \overline{\cos\Delta_i}}{\delta\cos\Delta_{ij}} \right]^2$$

In these expressions, $E_{MSE}$ represents minimum square error from mean, and $E_{MINMAX}$ represents minimum maximum deviation from mean. Each of $E_{MSE}$ and $E_{MINMAX}$ depends on "a" and "b" but not on $A_0$ (if the assumptions enumerated above are true).

The refined approximations of the values "a" and "b" (which determine the refined approximation of $P_0$) are those that minimize the selected error term (either $E_{EMS}$ or $E_{MINMAX}$). Since the characteristics of the error surface are unknown, the minimization procedure must allow for multiple local minima in the search region. The preferred technique is a global least squares function minimization. The straightforward procedure of locating the minima on a fine mesh and repeatedly refining each minimum on finer and finer meshes should suffice.

Having thus determined the refined approximation of $P_0$, the refined approximation of $A_0$ is determined as follows.

We define an error term to be one of $$E_{MSE} = \sum_i \sum_j \left[ \frac{\tan\Psi_{ij} - \overline{\tan\Psi_i}}{\delta\tan\Psi_{ij}} \right]^2$$

or $$E_{MINMAX} = \max_i \sum_j \left[ \frac{\tan\Psi_{ij} - \overline{\tan\Psi_i}}{\delta\tan\Psi_{ij}} \right]^2$$

In these expressions, $E_{MSE}$ represents minimum square error from mean, and $E_{MINMAX}$ represents minimum maximum deviation from mean.

Then, employing the refined approximations of the "a" and "b" values, the value of $A_0$ which minimizes the selected error term is identified as the refined approximation of $A_0$.

Another aspect of the invention is a spectroscopic ellipsometer including a means for automatically performing the calibration method of the invention. A preferred embodiment of such a spectroscopic ellipsometer will be described with reference to FIG. 4.

The spectroscopic ellipsometer of FIG. 4 includes processor 101 which is programmed to control analyzer 8 and polarizer 5 (and other components of the ellipsometer) appropriately, and perform the appropriate processing of the measured data received from detector array 173, to perform the inventive calibration method automatically.

The focused beam spectroscopic ellipsometer of FIG. 4 is identical to the ellipsometer described with reference to FIG. 1 of pending U.S. patent application Ser. No. 08/375,353 (filed Jan. 19, 1995), except in the following respect. The ellipsometer of FIG. 4 of the present disclosure includes programmed processor 101 rather than programmed processor 100 of the ellipsometer of U.S. application Ser. No. 08/375,353. The description in U.S. Ser. No. 08/375,353 of the FIG. 1 ellipsometer (and the details thereof and variations thereon described with reference to FIGS. 2–15 in U.S. Ser. No. 08/375,353) is incorporated herein by reference, since such description applies to the common features of the FIG. 1 ellipsometer of U.S. Ser. No. 08/375,353 (and the details thereof and variations thereon) and the FIG. 4 ellipsometer of the present disclosure (and the details thereof and variations thereon described in the present disclosure with reference to FIGS. 5–11).

In preferred implementations, processor 101 of FIG. 4 is programmed with calibration software in accordance with the invention, in addition to being programmed to perform all the functions performed by processor 100 in the FIG. 1 ellipsometer of U.S. application Ser. No. 08/375,353.

The spectroscopic ellipsometer of FIG. 4 includes several subsystems:

optical and signal processing components (components 1, 4–6, 6A, 7, 8, 10, 10A, 14, 16, 17, spectrometer components 69, 170, 171, 172, and 173, and processor 101) for measuring polarized radiation of beam 9 which has reflected from a small spot on sample 3, and for processing the measured data;

focusing and pattern recognition components (including objective 40 and subsystem 80) for controlling the focusing of beam 9 onto a desired small spot on sample 3, and optionally also for imaging sample 3 (or a selected portion of sample 3) and recognizing a pattern in such image; and sample stage 63 (for moving sample 3 relative to the ellipsometer's optical components and relative to objective 40).

Beam 9 (radiation emitted from lamp 10 and then polarized in polarizer 5) is reflected from sample 3 through a slit in aperture plate 6A to collection mirror 6, is then reflected from mirror 6 to mirror 7, and is then directed by mirror 7 through analyzer 8 into a spectrometer. The spectrometer (to be described in detail below) comprises entrance slit member 69, folding mirror 170, Ebert spherical mirror 171, prism 172, and detector array 173. Alternatively, an Ebert-Fastie or Czerny-Turner spectrometer can be employed.

Radiation (e.g., from lamp 10) is reflected from sample 3 back to objective 40, and is focused by objective 40 onto optical elements or sensors within subsystem 80 (for use in performing pattern recognition, controlling the focusing of beam 9 onto sample 3, and optionally displaying an image of all or part of the sample). Sample 3 is typically a semiconductor wafer with at least one thin layer 3a on a substrate.

The illumination subsystem of FIG. 4 includes lamp 10 (preferably a xenon arc lamp including heatsink window 10A) which emits radiation beam 12 having a broad range of frequency components in the UV, visible, and near infrared wavelength bands, a lamp housing including lamp housing window 14, off-axis paraboloid mirror 16, UV cutoff filter 18 and color filter 20, paraboloid mirror 17, and optical fiber 1. Fiber 1 has an inlet end for receiving beam 12, after beam 12 has reflected from mirror 16, passed through UV cutoff filter 18 and color filter 20, and then reflected from mirror 17. Beam 12 propagates through fiber 1 to entrance slit member 2 and then through the entrance slit in member 2. Mirrors 16 and 17 preferably have identical design.

Lamp 10 emits beam 12 through heatsink window 10A and then through lamp housing window 14, to mirror 16. Windows 10A and 14 are unnecessary for optical reasons, but function to keep lamp cooling air from being drawn through the optical path, thereby avoiding noise due to shimmering of the arc image. A xenon arc lamp is preferred over other lamps such as tungsten or deuterium lamps, because a xenon lamp will produce radiation having a flatter spectrum in the wavelength range from UV to near infrared. Alternatively, a tungsten lamp and a deuterium lamp can be used in combination to cover the substantially the same spectrum covered by a xenon lamp. Brightness of the spectrum is important, because with less intensity, reflected radiation must be collected for longer periods. The lower intensities slow the measurement process. In alternative embodiments, a lamp is chosen which emits broadband UV radiation without emitting significant visible or near infrared radiation.

Preferably, optical fiber 1 is made of fused silica, a UV transmitting material, and has a core diameter of 365 microns.

The illumination subsystem optionally includes actuator 17A connected to mirror 17. Actuator 17A operates to move mirror 17 between a first position (shown in FIG. 4) in which it reflects beam 12 from mirror 16 toward the inlet end of fiber 1, and a second position (not shown in FIG. 4). In such second position, mirror 17 is outside the optical path of beam 12 and thus does not impede propagation of beam 12 from mirror 16 to a spectrophotometer. Such spectrometer is not shown in FIG. 4, but is preferably integrated with the ellipsometer.

With reference again to FIG. 4, the sample illuminating radiation enters polarizer 5 after propagating from fiber 1 through the entrance slit in member 2. The portion of this radiation which propagates through polarizer 5 emerges from polarizer 5 as polarized beam 9. Polarized beam 9 is a measurement beam having a known polarization state. Polarizer 5 preferably has apertured plate 5A, with a circular aperture therethrough, positioned at its input face to limit the size of the polarized beams so that the two polarizations do not overlap. The diameter of this circular aperture is about 1 mm in one preferred embodiment in which the distance between entrance slit member 2 and polarizer 5 is about three inches.

Entrance slit member 2 is a substrate (preferably made of stainless steel) through which an elongated, rectangular entrance slit (60 microns×500 microns) has been etched. Because of the elongated shape of the entrance slit, elliptical focusing mirror 4 images the entrance slit as a small (25 micron×25 micron), compact (square-shaped) spot on sample 3, by reflectively focusing the beam 9 onto sample 3 at high incidence angle. Polarized beam 9 is incident at mirror 4 with a low incidence angle. Due to its orientation and the shape of its elliptical focusing surface, mirror 4 images the entrance slit. Mirror 4 has a numerical aperture (0.15 or greater, in preferred implementations of FIG. 4) selected so that the rays of beam 9 reflected from mirror 4 will be incident at sample 3 with a desired range (preferably, a substantial range) of high incidence angles. In preferred implementations of FIG. 4 in which the numerical aperture of mirror 4 is 0.15, the range of high incidence angles (at which beam 9 strikes sample 3) is the range from about 63.5 degrees to about 80.5 degrees (from the normal to the surface of sample 3). This range desirably includes incidence angles near Brewster's angle for crystalline silicon (about 75° at 630 nm wavelength) so that the instrument displays a high degree of sensitivity for film variations on silicon substrates.

The preferred shape of focusing mirror 4's reflective surface is elliptical. As is well known, an elliptical mirror has two foci. In embodiments in which mirror 4 is an elliptical mirror, sample 3 should be positioned at one focus of the mirror and the entrance slit (through member 2) should be positioned at the other focus of the mirror.

The elongated shape of the entrance slit in member 2, with the described design and orientation of mirror 4, results in focusing of beam 9 onto a small, compact (preferably square-shaped) spot on sample 3 with high incidence angle.

In alternative embodiments, other combinations of an entrance slit and a focusing mirror are employed (in place of elements 2 and 4 of FIG. 4) to focus a beam onto a small (but not compact) spot on sample 3 with a substantial range of high incidence angles.

Designing the reflective surface of mirror 4 to have its preferred elliptical shape (rather than a spherical shape, for example) reduces off-axis aberrations (such as the aberration known as "coma") in the focused beam incident on the sample. Use of a reflective elements (mirrors 4, 6, and 7) between the polarizer and analyzer, rather than transmissive lenses, minimizes chromatic aberration in the analyzed beam which reaches spectrometer entrance slit member 69.

Collection mirror 6 receives that portion of the diverging beam reflected from sample 3 which passes through an aperture in apertured plate 6A. Mirror 6 preferably has a focal length of 70 mm and a diameter of 20 mm. Mirror 6, because it is spherical, introduces coma into the beam. However, the aberration spreads the beam in a direction parallel to the long axis of the spectrometer entrance slit so it does not affect the light transmission properties of the instrument. In addition the spectrometer entrance slit is preferably rotated by approximately 5 degrees in a plane perpendicular to the surface normal in order to better pass the aberrated beam.

The aperture in plate 6A is preferably elongated, and oriented to pass only the radiation which has reflected from sample 3 after reaching the sample at a single incidence angle (or narrow range of incidence angles). The aperture is preferably about 2 mm tall (in the Z-direction shown in FIG. 4) and 20 mm wide, and oriented so as to pass the radiation reflected from sample 3 at an angle in the range from 75° to 77°, while plate 6A blocks all other radiation reflected from sample 3. Thus, where beam 9 strikes sample 3 with a substantial range of high incidence angles, apertured plate 6A passes (for propagation to analyzer 8 and then measurement by detector 173) only the radiation reflected from sample 3 after striking the sample at a narrow subset of the substantial range of high incidence angles.

Actuator 62 can position plate 6A at any selected one of a range of positions in the optical path of reflected beam 9, so that the slit (aperture) through plate 6A will pass only those rays of the reflected beam which have reflected from sample 3 at incidence angles in a selected narrow range. For example, actuator 62 can be operated to move plate 6A (downward along the Z-axis in FIGS. 4 and 9) from the position shown in FIG. 4 (and FIG. 9) to a position in which the slit through plate 6A passes radiation reflected from sample 3 at an angle in the range from 77° to 79° (and in which plate 6A blocks all other radiation reflected from the sample). Plate 6A and actuator 62 are shown in both FIGS. 4 and 9, but the manner in which plate 6A blocks some of the radiation reflected from sample 3 is shown more clearly in FIG. 9.

To measure a complicated film stack, it is necessary to perform multiple independent measurements at different settings of one or more measurement parameters (such as wavelength or incidence angle). Spectroscopic ellipsometric measurement (at a fixed incidence angle) simultaneously provides data for multiple wavelengths of radiation reflected from the sample. Varying incidence angle in a sequence of spectroscopic ellipsometric measurements provides data about the sample which usefully supplements the data obtained at one fixed incidence angle.

The width of the slit through apertured plate 6A determines the spreading of the incidence angles associated with the measured portion of the radiation reflected from sample 3, and the location of the slit's center determines the average incidence angle associated with the measured portion of such reflected radiation. Preferably, actuator 62 includes means for controlling both the slit width and the location of the slit's center. However, in some embodiments of the invention, the slit width and/or the location of the slit center are fixed. In embodiments in which the location of the slit center can be controlled, such location will typically be chosen to be close to Brewster's angle for the sample being measured. For example, when the sample is a flat panel display comprising films deposited on a glass substrate, it is useful to locate the slit center so that plate 6A passes only rays reflected from the flat panel display after being incident at angles in a narrow range centered at 57° (since Brewster's angle for glass is about 57° at visible wavelengths). The latter embodiment would require substitution of a differently shaped focusing mirror for above-described elliptical focusing mirror 4 (since above-described mirror 4 could not focus radiation to sample 3 at incidence angles close to 57 degrees).

Figure 7:
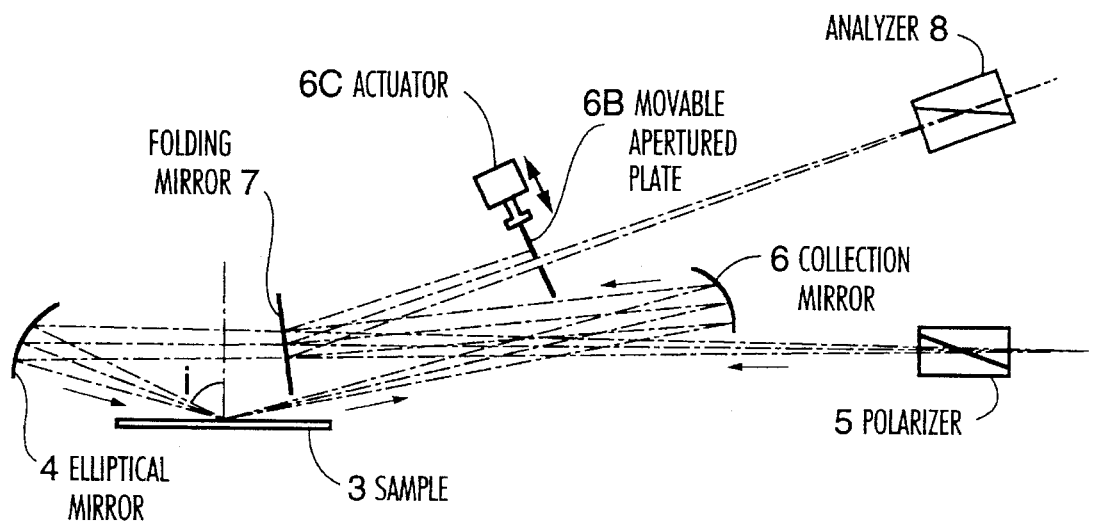
FIG. 7 is a schematic diagram of a portion of a variation on the ellipsometer of FIG. 4.

Apertured plate 6A functions as an incidence angle selection element. An alternative position for the incidence angle selection element is shown in FIG. 7, and another such alternative position is between mirror 6 and mirror 7. In FIG. 7, the incidence angle selection element is movable apertured plate 6B, which is located between folding mirror 7 and analyzer 8. Actuator 6C of FIG. 7 controls the location of the center of the slit through plate 6B, so that when radiation reflected from sample 3 at a substantial range of angles reaches plate 6B, only a portion of such radiation (i.e., the radiation reflected from sample 3 at a selected, narrow subrange of the "substantial range") will pass through plate 6B's slit. The dimensions of apertured plate 6B and the slit therethrough can (but need not) be identical to those of apertured plate 6A. Actuator 6C can (but need not) be identical to actuator 62 of FIG. 4.

Figure 8:
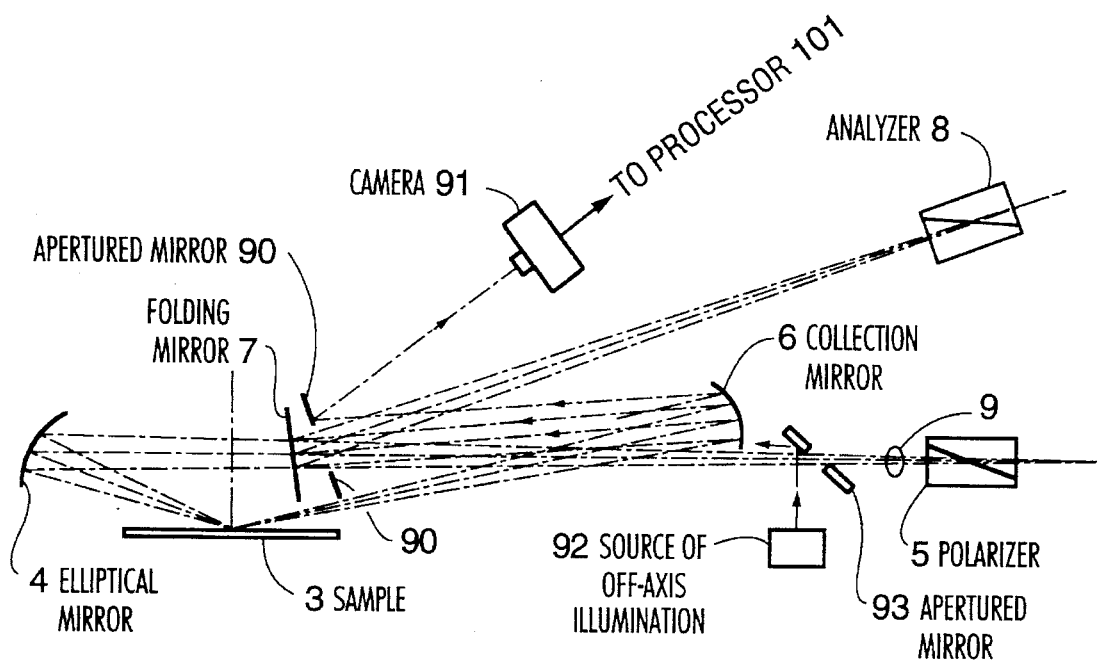
FIG. 8 is a schematic diagram of a portion of another variation on the ellipsometer of FIG. 4.
Figure 9:
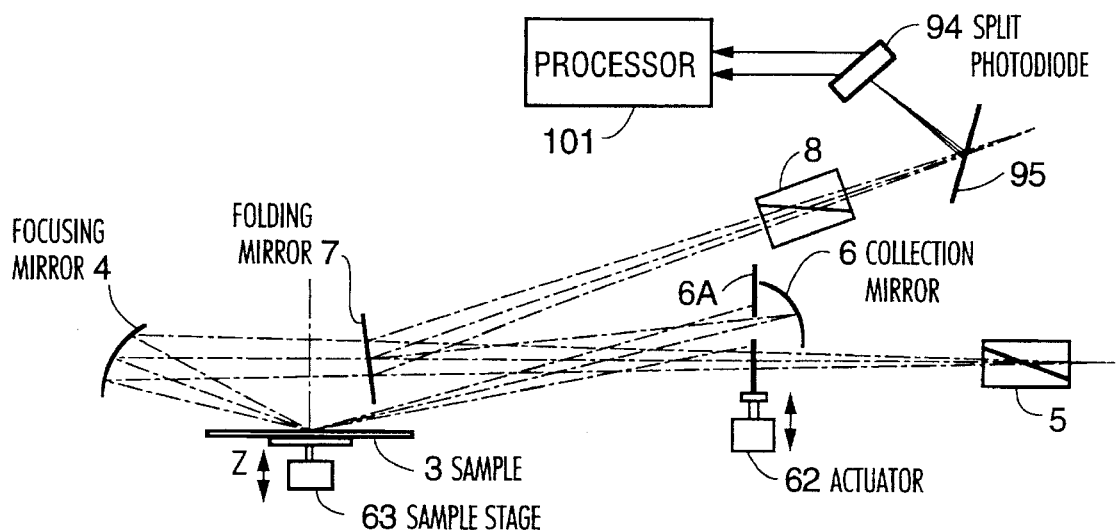
FIG. 9 is a schematic diagram of a portion of another variation on the ellipsometer of FIG. 4.

It should be understood that in each of FIGS. 7, 8, and 9, the polarized beam emitted from polarizer 5 propagates directly to mirror 4 without interacting with mirror 7. Mirror 7 is positioned so as to reflect (toward analyzer 8) only radiation that has already reflected from mirror 6.

With reference again to FIG. 4, either polarizer 5 or analyzer 8 is rotated (about the optical axis) during measurement operations (including calibration operations). When polarizer 5 is to be rotated and analyzer 8 to remain fixed, each of polarizer 5 and analyzer 8 is preferably a minimal-length Rochon prism of the type shown in FIGS. 5 and 6. The Rochon prism consists of two pieces separated by interface 5C, and splits the incident beam into two components: an ordinary polarized through beam, and an extraordinary polarized beam that is deflected by an angle of 1.6 degrees (a deflection of at least 1.5 degrees is preferred for implementing the invention). The ordinary polarized beam is employed as beam 9 (which is focused by mirror 4 on the sample). Since it is desired to focus beam 9 on a small spot on the sample (e.g., to measure film thickness at such spot), no motion in the ordinary polarized "through" beam emitted from prism 5 can be tolerated. Typically, the rotation of prism 5 must be controlled so that the through beam deviation is constrained to be less than 30 seconds of arc, in order to restrict the motion of the spot on the sample to less than 1 micron. In some cases, through beam deviation of up to one minute of arc can be tolerated.

With reference to FIGS. 5 and 6, the preferred Rochon prism embodiment of polarizer 5 (and analyzer 8) has only the minimum length (along the axis of "through beam" propagation) needed to enable the beam to pass through its clear aperture, because the prism's length is proportional to the amount of chromatic aberrations introduced by the prism.

The area within polarizer 5 bounded by rectangular perimeter 5D in FIG. 5 is the projection of interface 5C onto the plane of FIG. 5, and is what is referred to as the "clear aperture" of polarizer 5. As shown in FIG. 4, plate 5A having an entrance aperture therethrough should be positioned along the optical path between entrance slit element 2 and polarizer 5, so that the aperture through plate 5A determines the diameter of the beam (which has passed through the entrance slit through element 2) which passes through polarizer 5. The length of polarizer 5 should be the minimum length (assuming a fixed angle between interface 5C and the right face of polarizer 5 in FIG. 6) which causes the clear aperture to be as large as the cross-section of the beam incident on polarizer 5. It will be apparent to those of ordinary skill that the mechanical constraints inherently faced in designing and mounting a polarizer will also affect the minimum practical length for polarizer 5, and that varying the position of prism 5 (in the FIG. 4 system) will affect the preferred size of the aperture through plate 5A.

Rochon prism 5 of FIG. 6 (which is preferred for use as polarizer 5 and analyzer 8 in FIG. 4) has a length (along the axis of through beam propagation) equal to 12 mm, with a tolerance of plus or minus 0.25 mm. In contrast, the length of a conventional, commercially available Rochon prism 5' (shown in phantom view in FIG. 6) is approximately 25 mm. As shown in FIG. 5, the Rochon prism 5 preferred for use as polarizer 5 in FIG. 4, has a square cross-section (in a plane perpendicular to the axis of through beam propagation) with sides of length 8 mm, with a tolerance of plus or minus 0.1 mm. The preferred Rochon prism of FIGS. 5 and 6 preferably uses UV transmitting crystalline quartz, is optically contacted for enhanced UV transmission, introduces wavefront distortion of less than one quarter of a wavelength (at 633 nm), has transmittance in the UV of at least 40% (for two open polarizers at 230 nm) when used with an unpolarized light source, and has uncoated faces.

To measure a sample, analyzer 8 typically remains fixed while polarizer 5 rotates about the optical axis. Analyzer 8 is mounted so as to be free to rotate into a different angular orientation when a new sample is placed in the instrument (or when a new measurement is to be conducted on the same sample). This technique of "analyzer tracking" is well known in the field of ellipsometry.

To implement the inventive calibration method, processor controls operation of the FIG. 4 spectroscopic ellipsometer as follows. Processor 101 generates control signals, and supplies them to polarizer 5, analyzer 8, and detector array 173 to control acquisition by detector array 173 of data of the type described above with reference to equations (10)–(15), and then receives this data from array 173 and processes the data to determine coarse approximations of the above-defined values $A_0$ and $P_0$. For example, in some embodiments processor 101 is programmed to generate a sequence of the control signals for rotating analyzer 8 into a sequence of different fixed positions at appropriate times during measurement of the data, and for causing polarizer 5 to rotate with appropriate substantially constant speed during measurement of the data.

In the FIG. 4 embodiment, $P_0$ is the angle between the optical axis of polarizer 5 and the plane of incidence at t=0, and $A_0$ is the offset of the actual orientation angle of analyzer 8 from the nominal angle A of analyzer 8 (where "A" is a reading of analyzer 8's orientation angle, supplied to processor 101, for example, from an analyzer position sensor associated with analyzer 8). To control acquisition of this data, processor 101 generates control signals for controlling the orientation of analyzer 8 and the rotation of polarizer 5 (and the operation of the other system components) to cause detector array 173 to provide to processor 101 the data to be processed in accordance with equations (10)–(15).

After determining the coarse approximations of $A_0$ and $P_0$, processor 101 generates control signals for controlling the orientation of analyzer 8 and the rotation of polarizer 5 (and the operation of the other system components) to cause detector array 173 to provide to processor 101 the necessary data to be processed to determine the refined approximations of $A_0$ and $P_0$ in accordance with the inventive method. More specifically, processor 101 generates control signals to cause detector array 173 to provide reflectivity data (tanψ and cosΔ spectra) at each of two or more angles of analyzer 8, and processor 101 then performs regression on this data to determine the refined approximations of the values $A_0$ and $P_0$. The reflectivity data (for each angle of analyzer 8) consist of a sequence of readings of detector array 173 taken while polarizer 5 rotates, with each read-out of detector array 173 made at a different angular position of polarizer 5. The reflectivity data determine a tan$\psi$ spectrum and a cos$\Delta$ spectrum for each of at least two analyzer angles, each set of reflectivity data measured by operating the ellipsometer (with rotating polarizer 5) at a different angle of analyzer 8. The tan$\psi$ and cos$\Delta$ spectra for each analyzer angle determine the amplitude and phase of the complex ratio of p and s components of the reflectivity of sample 3 (at each of at least two incident radiation frequencies).

Alternative embodiments of the FIG. 4 system employ an alternative type of polarizer (and analyzer), such as a Glan-Taylor polarizer. Other embodiments employ a phase modulator (such as a photoelastic modulator) in place of a rotating polarizer.

In other embodiments, the invention is a method for calibrating a spectroscopic ellipsometer (or other ellipsometer) whose analyzer rotates during measurement of a sample, and whose polarizer (which can be a minimal-length polarizer or other polarizer) remains fixed during each measurement of a sample. Another aspect of the invention is an ellipsometer of this type which includes a means for performing the calibration method automatically (preferably including a processor programmed with software for performing the calibration method automatically). In these embodiments, the above-described calibration method of the invention is modified in a manner that will be apparent to those of ordinary skill in the art so that it determines coarse (and then refined) approximations of values $P'_0$ and $A'_0$, where $A'_0$ is the angle (at t=0) of the optical axis of the analyzer, and $P'_0$ is the offset of the actual orientation angle of the fixed polarizer from the nominal (measured) angle P' of the fixed polarizer.

To understand this modified method, it is should be appreciated that when the analyzer is controlled so that it rotates at a constant speed, the signal received at the detector (or each detector of the detector array of a spectroscopic ellipsometer) will be a time-varying intensity given by:

$$I(t) = I_0[1 + \alpha \cos(2\omega t - A'_0) + \beta \sin(2\omega t - A'_0)] \quad (1')$$
$$= I_0[1 + \alpha' \cos(2\omega t) + \beta' \sin(2\omega t)]$$

where $I_0$ is a constant that depends on the intensity of radiation emitted by the source, $\omega$ is the angular velocity of the analyzer, $A'_0$ is the angle of the optical axis of the analyzer at an initial time (t=0), and $\alpha$ and $\beta$ are sample related values defined as follows:

$$\alpha = [\tan^2\psi - \tan^2(P'-P'_0)]/[\tan^2\psi + \tan^2(P'-P'_0)] \quad (2')$$

and $$\beta = 2(\tan\psi)(\cos\Delta)\tan(P'-P'_0)/[\tan^2\psi + \tan^2(P'-P'_0)] \quad (3')$$

where tan$\psi$ is the amplitude of the complex ratio of the p and s components of the reflectivity of the sample, $\Delta$ is the phase of the complex ratio of the p and s components of the reflectivity of the sample, P' is the nominal polarizer angle (a reading of the polarizer's orientation angle, supplied for example from a sensor which senses the position of the polarizer), and $P'_0$ is the offset of the actual orientation angle of the polarizer from the nominal polarizer angle "P'."

The values $\alpha'$ and $\beta'$ are also sample related values, defined as follows:

$$\alpha' = \alpha\cos(2A'_0) + \beta\sin(2A'_0) \quad (4')$$

and $$\beta' = \alpha\sin(2A'_0) - \beta\cos(2A'_0) \quad (5')$$

where $\alpha$, $\beta$, and $A'_0$ are defined above.

In embodiments in which ellipsometer measures reflectivity data with a rotating analyzer and fixed polarizer, the inventive calibration method determines (from reflectivity data measured using the ellipsometer) the same "residual" (R) defined above in equation (6): $R = 1 - \alpha^2 - \beta^2 = 1 - \alpha'^2 - \beta'^2 = R'$. To calibrate such an ellipsometer, the inventive method determines the coarse approximations of $A'_0$ and $P'_0$ as follows.

First, data determining nominal residual value $R'(P'_1)$ are acquired with the fixed polarizer at a first nominal polarizer angle $P'_1$. This is done by exploiting symmetry (without knowledge of values $A'_0$ and $P'_0$), assuming for purposes of determining the nominal value $R'(P'_1)$ that $P_0=0$.

Also, data determining nominal values $R'(P'_i)$ are acquired at several nominal polarizer angles $P'_i$, all approximately equal to $-P'_1$.

The next step exploits the fact that the actual value $R'$ satisfies the symmetry relation $R'(P'-P'_0) = R'[-(P'-P'_0)]$. In this step, the invention determines a second nominal polarizer angle $P'_2$ at which the nominal value $R'(-P'A_2)$ is closest to the nominal value $R'(P'_1)$. The second nominal angle $P'_2$, which has the same sign as the first nominal angle $P'_1$, is equal to $P'_2 = -P'_{i1}$, where $+P'_{i1}$ is one of the nominal polarizer angles $P'_i$ that are approximately equal to $-P'_1$.

Then, the invention averages the two nominal angles $P'_2$ and $P'_1$, and identifies the resulting averaged value (shown in equation (10')) as the coarse approximation of $P'_0$:

$$P'_0 = (P'_1 + P'_2)/2 \quad (10')$$

Using this coarse approximation of $P'_0$, the coarse approximation of $A'_0$ is determined as follows. From equations (2') and (3'), it follows that:

$$\alpha_+ = \alpha(P'-P'_0) = \alpha[-(P'-P'_0)] = \alpha_- \quad (11')$$

and $$\beta_+ = \beta(P'-P'_0) = -\beta[-(P'-P'_0)] = -\beta_- \quad (12')$$

We denote $\alpha'(P'-P'_0)$ as $\alpha_+'$, $\alpha'[-P'-P'_0]$ as $\alpha_-'$, $\beta'(P'-P'_0)$ as $\beta_+'$, and $\beta'[-(P'-P'_0)]$ as $\beta_-'$. From equations (11'), (12'), (4'), and (5'), it follows that:

$$\alpha_+' + \alpha_-' = 2\alpha\cos(2A'_0) \quad (13')$$

and $$\beta_+' + \beta_-' = 2\alpha\sin(AP'_0) \quad (14')$$

Thus, the coarse approximation of $A'_0$ is determined to be $$A'_0 = \tan^{-1}[(\beta_+' + \beta_-')/(\alpha_+' + \alpha_-')]/2 \quad (15')$$

Having determined coarse approximations of the values $A'_0$ and $P'_0$, the invention then determines refines approximations of the coarsely approximated values $A'_0$ and $P'_0$, in the following manner. First, the ellipsometer (undergoing calibration) is operated to measure reflectivity data at each of two or more polarizer angles (with a rotating analyzer and fixed polarizer at each of the polarizer angles). The reflectivity data (for each polarizer angle) determine both a tan$\psi$ value and a cos$\Delta$ value for each incident radiation frequency (data for two or more frequency components are measured where the ellipsometer is a spectroscopic ellipsometer). In the case that the ellipsometer is a spectroscopic ellipsometer, the reflectivity data for each polarizer angle determine $\tan\psi$ and $\cos\Delta$ spectra, which in turn determine the amplitude and phase of the complex ratio of p and s components of sample reflectivity (at each incident radiation frequency).

The reflectivity data (e.g., $\tan\psi$ and $\cos\Delta$ spectra) obtained at multiple polarizer angles are then processed to determine refined approximations of the values $A'_0$ and $P'_0$. Preferably, the reflectivity data are processed by performing regression on $A'_0$ and $P'_0$ (using the well-known least square fit algorithm or another function minimization technique, in a class of preferred embodiments) until the differences among the reflectivity data for different polarizer angles are minimized.

With reference again to FIG. 4, the spectrometer subsystem of the FIG. 4 embodiment of the inventive spectroscopic ellipsometer will next be described. This subsystem comprises entrance slit member 69, folding mirror 170, Ebert spherical mirror 171, prism 172, and detector 173. Slit member 69 is made of the same material as above-described entrance slit member 2. The spectrometer entrance slit through member 69 is preferably an elongated slit of size 230 microns by 1200 microns (the beam is focused to a spot on sample 3 which is smaller than this entrance slit, and so the beam passes through the entrance slit unobstructed). The spectrometer is of a standard Ebert design, in which the broadband beam passed through member 69 (from analyzer 8) reflects from mirror 170 to mirror 171, and from mirror 171 to prism 172. The beam components having different wavelengths are refracted in different directions from prism 172 to mirror 171, and from mirror 171 to detector 173. Mirror 171 images the entrance slit (through member 69) to detector 173, and mirror 171 preferably has a focal length of 250 mm. In preferred embodiments, detector 173 is essentially a linear array of photodiodes, with each photodiode measuring radiation in a different wavelength range. Preferably the radiation includes components with wavelength in the range from 230 nm to 850 nm, detector array 173 includes 512 photodiodes, and each photodiode (or set of adjacent photodiodes) receives radiation in a different segment of the 230–850 nm wavelength range. For example, the resolution of the photodiode array may be limited to groups of three to five adjacent photodiodes, in the sense that each resolvable radiation element has a width of three to five photodiodes.

Preferably, detector array 173 is an intensified photodiode array. For example, it can be a photodiode array available from the Japanese company Hammamatsu, to which an intensifier, known as Part Number BV2532QZ-15 available from Proxitronics, is mated. The photodiode array of this commercially available product has 512 photodiodes, which independently measure 512 different wavelengths. An alternative embodiment of detector array 173 is a UV enhanced CCD array detector.

We next describe two embodiments of an autofocus assembly for the inventive ellipsometer. One such assembly is shown in FIG. 8, and the other will be described with reference to FIGS. 9 and 10.

Figure 10:
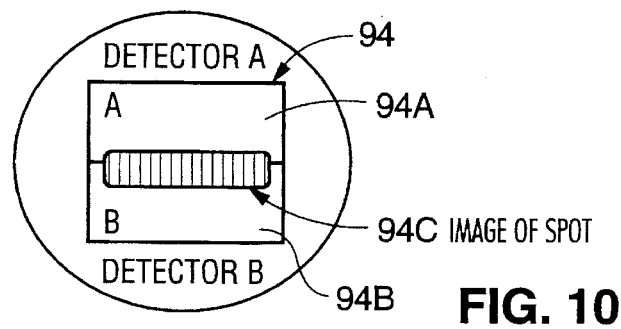
FIG. 10 is a front elevational view of detector 94 of FIG. 9.

The autofocus assembly of FIGS. 9 and 10 includes split photodiode detector 94, which receives a substantially focused image of the spot to which beam 9 is focused on sample 3. This image is provided by positioning beamsplitting mirror 95 along the optical path between analyzer 8 and spectrometer entrance slit element 69 (of FIG. 4) to divert a portion of the beam transmitted through analyzer 8 to detector 94. Detector 94 has two photodiodes, 94A and 94B, which are best shown in FIG. 10. Each of photodiodes 94A and 94B provides a measured intensity signal to processor 101. Processor 101 is programmed to be capable of processing these signals in the same manner (described in U.S. patent application Ser. No. 08/375,353) as does processor 100 of U.S. application Ser. No. 08/375,353. Detector 94 is positioned so that an entire substantially focused image (94C) of the spot can be projected onto photodiodes 94A and 94B, with approximately half of image 94C projected onto each of photodiodes 94A and 94B as shown in FIG. 10.

The auto focus system of FIGS. 9–10 (and its method of operation) is fast (i.e., processor 101 determines the necessary values very quickly); the algorithm implemented by processor 101 is simple; and this auto focus system gives directional information (in the sense that it enables the operator to tell whether the sample is above or below the best focus position).

In designing the autofocus assembly of FIGS. 9–10, it is important to consider that the image intensity seen by the camera is time-varying, and that the speed at which the video image can be digitized and processed should be sufficiently high to enable autofocus, The alternative autofocus assembly of FIG. 8 includes source 92 of off-axis illuminating radiation, apertured mirror 93, apertured mirror 90, and camera 91. Apertured mirror 90 has a slit extending through it, and functions as an incidence angle selection element similar to the way apertured plate 6B of FIG. 7 functions as an incidence angle selection element. Indeed mirror 90 can be of identical design as apertured plate 6B (but the planar surface of mirror 90 which faces away from mirror 7 is highly reflective, while the corresponding planar surface of plate 6B need not be highly reflective). A first portion of the radiation from collection mirror 6 passes through the slit in mirror 90, and then reflects from mirror 7 toward analyzer 8 (just as in FIG. 4 and FIG. 7). However, because mirror 90 is tilted at a small angle with respect to folding mirror 7 (and is positioned along the optical path), mirror 90 reflects a second portion of the radiation that it receives from collection mirror 6 toward camera 91 (this second portion does not pass through the slit in mirror 90, and does not propagate to analyzer 8). The radiation reflected from mirror 90 is focused to camera 91, and camera 91 thus observes the position and size of the spot on sample 3.

Signals indicative of the position and size of the spot are supplied from camera 91 to processor 101. In response to these signals, processor 101 generates focus control signals (in the same manner as does processor 100 of U.S. Ser. No. 08/375,353) that are used for focusing the sample (e.g., the focus control signals are used for controlling the position of sample stage 63). Where camera 91 is part of focusing and pattern recognition subsystem 80 of FIG. 4, the signals output from camera 91 are used for pattern recognition as well as for the auto focus function described with reference to FIG. 8.

Apertured mirror 93 has an aperture therethrough which allows polarized beam 9 from polarizer 5 to pass unimpeded to mirror 4. Apertured mirror 93 also reflects off-axis illuminating radiation from source 92 toward mirror 4. This off-axis illuminating radiation is reflected to camera 91, where it enables camera 91 to "see" the position of the spot to which beam 9 is focused on the sample (and to enable pattern recognition and auto focus operations).

Figure 11:
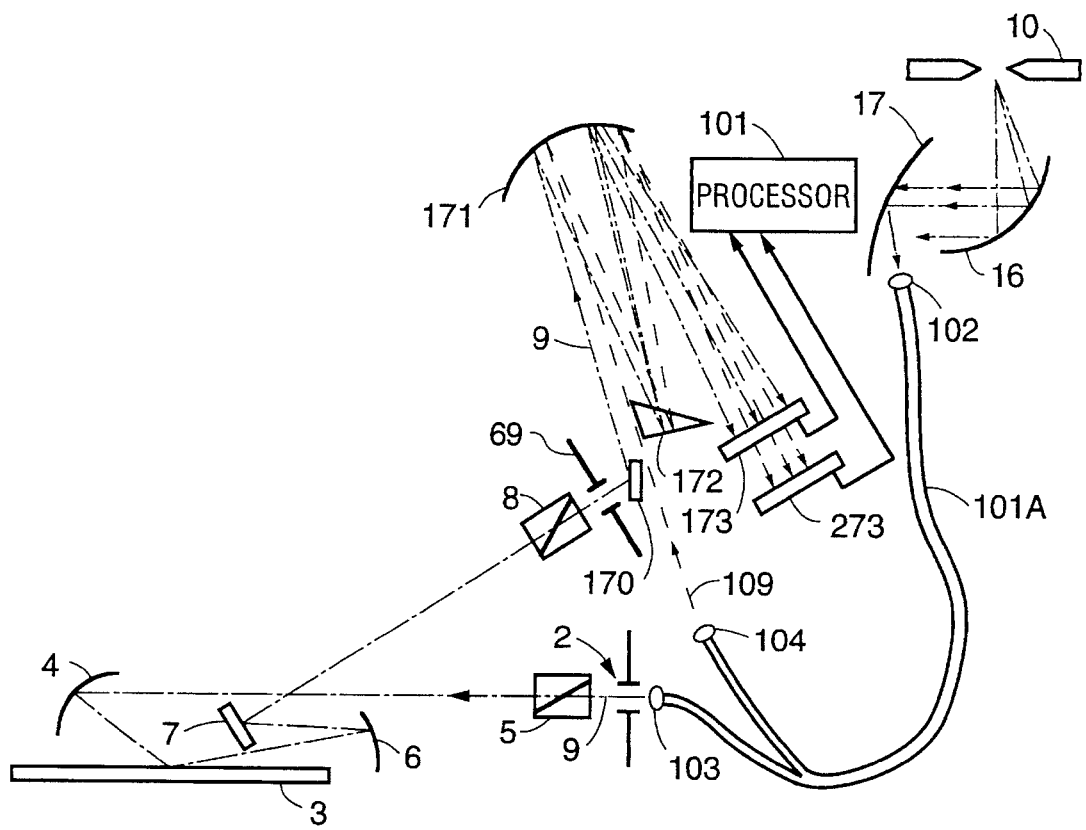
FIG. 11 is a schematic diagram of another variation on the ellipsometer of FIG. 4, which detects a reference beam, as well as a sample beam after the sample beam has reflected from a sample.

Next, with reference to FIG. 11, we describe embodiments in which the inventive ellipsometer includes a reference channel (in addition to a sample channel which detects radiation reflected from the sample). The ellipsometer of FIG. 11 has both a reference channel (including detector array 273) and a sample channel (including detector array 173). Illuminating radiation from lamp 10 reflects from mirror 16 to mirror 17, and then from mirror 17 to entrance end 102 of bifurcated optical fiber 101A. As the radiation propagates within fiber 101A away from end 102, it is split into two portions: a reference beam 109 emitted from end 104 of fiber 101A; and sample beam 9 (identical to beam 9 of FIG. 4) emitted from end 103 of fiber 101A. Sample beam 9 is polarized in rotating polarizer 5, then is reflectively focused by mirror 4 to sample 3, then reflects from the sample surface to mirror 6 and then mirror 7, and then reflects from mirror 7 through analyzer 8 to the entrance slit in spectrometer entrance slit member 69. In the spectrometer, the portion of sample beam 9 passed through member 69 reflects from mirror 170 to mirror 171, and from mirror 171 to prism 172. The beam components having different wavelengths are refracted in different directions from prism 172 to mirror 171, and from mirror 171 to sample channel detector array 173.

Reference beam 109 does not reflect from sample 3, but is directed directly to the spectrometer. Specifically, beam 109 reflects from mirror 171 (i.e., from a slightly different spot on mirror 171 than the spot from which beam 9 reflects) to prism 172. The components of beam 109 having different wavelengths are refracted in different directions from prism 172 to mirror 171, and from mirror 171 to reference channel detector array 273. Detector arrays 173 and 273 are identical, but have slightly offset positions, so that the former receives only radiation of beam 9 reflected from mirror 171, and the latter receives only radiation of beam 109 reflected from mirror 171.

Alternatively, a plate with a double entrance slit is substituted for plate 69 of FIG. 11. In such embodiments, the sample beam passes through one entrance slot into the spectrometer and the reference beam passes through the other entrance slot into the spectrometer.

By processing reference signals from reference channel detector array 273 with signals from sample channel detector array 173, the thickness (or refractive index) of a thin film on sample 3 can (under some conditions) be more accurately determined than with the FIG. 4 ellipsometer (which has no reference channel). In the In the FIG. 11 system, processor 101 is programmed (in the same manner as is processor 100 of U.S. application Ser. No. 08/375,353) to normalize the reflectivity measured by sample beam 9 using the reference beam measurements from detector array 273, to compensate for such effects as lamp intensity fluctuations and air currents.

An alternative technique for obtaining a reference beam is to modify the FIG. 4 apparatus so that it splits beam 9 at the location of focus mirror 4. This can be done by designing mirror 4 to have a more complicated shape which focuses a portion of beam 9 (which functions as the sample beam) to sample 3 and directs the remaining portion of beam 9 (the reference beam) directly to collection mirror 6. In this case, the shape of collection mirror 6 would also be modified to reflect the reference beam to a separate channel in the spectrometer, while directing the sample beam to mirror 7.

Other variations on the FIG. 4 ellipsometer will include a second optical fiber, identical to fiber 1, for directing the radiation propagating out from analyzer 8 to the spectrometer entrance slit through member 69. Alternatively, the inventive ellipsometer can omit fiber 1, and include only one optical fiber which directs radiation from analyzer 8 to the spectrometer entrance slit.

Several variations on the spectroscopic ellipsometer of FIG. 4 have been described with reference to FIGS. 5–11. In other alternative embodiments of the inventive ellipsometer, polarized radiation having only one wavelength (rather than broadband radiation) is reflected from the sample. These embodiments can include a spectrometer as in FIG. 4, or alternatively a simple photodiode detector which detects the radiation output from the analyzer. In the alternative embodiments which employ a simple photodiode detector (rather than a spectrometer including a detector array), the ellipsometer is not a "spectroscopic ellipsometer."

Figure 12:
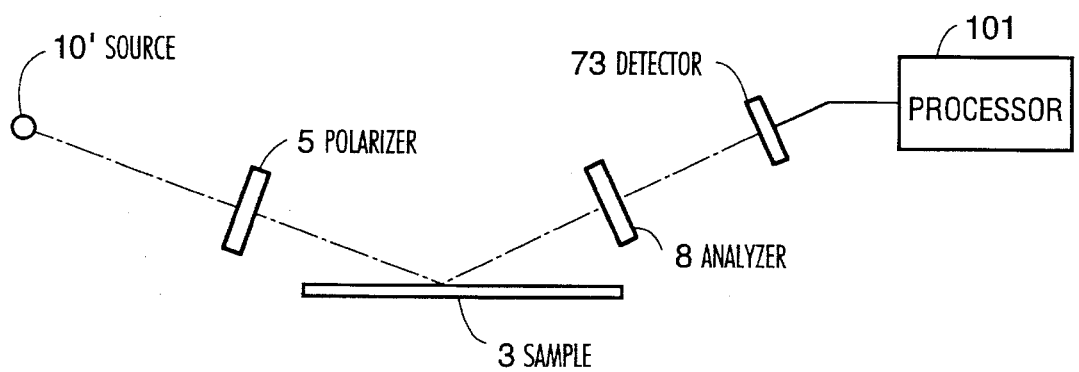
FIG. 12 is a schematic diagram of an ellipsometer (not a spectroscopic ellipsometer) which includes means (including a programmed processor) for performing an embodiment of the inventive calibration method automatically.

FIG. 12 is a schematic diagram of an ellipsometer (not a spectroscopic ellipsometer) which includes a means for performing an embodiment of the inventive calibration method automatically. In operation of the FIG. 12 ellipsometer, a beam of radiation (which can be monochromatic radiation) from radiation source 10' is linearly polarized in polarizer 5, and the linearly polarized beam is then incident on sample 3. After reflection from sample 3, the beam propagates toward analyzer 8 with a changed polarization state (typically, the reflected beam has elliptical polarization, where the polarized beam emerging from polarizer 5 had linear polarization). The reflected beam propagates through analyzer 8 to photodiode detector 73. Detector 73 outputs a signal indicative of the intensity of a single frequency component (or frequency components in a single frequency range) of the radiation incident thereon. Processor 101' receives the measured data from detector 73, and is programmed with software for processing the data it receives in an appropriate manner. Either polarizer 5 or analyzer 8 is rotatably mounted for rotation about the optical axis during a measurement operation (or both of them are so rotatably mounted). During a typical measurement operation, polarizer 5 is rotated and analyzer 8 remains in a fixed orientation, or analyzer 8 is rotated and polarizer 5 remains fixed.

Processor 101' is programmed to generate control signals for controlling the rotation (or angular orientation) of polarizer 5 and/or analyzer 8, or for controlling other operating parameters of elements of the FIG. 12 system (such as the position of a movable sample stage on which sample 3 rests). Processor 101' also receives data (indicative of the angular orientation of analyzer 8) from an analyzer position sensor associated with analyzer 8 and data (indicative of the angular orientation of polarizer 5) from a polarizer position sensor associated with polarizer 5, and is programmed with software for processing such orientation data in an appropriate manner.

To calibrate an ellipsometer (which is not a spectroscopic ellipsometer) such as that of FIG. 12 in accordance with the invention, for operation with a fixed analyzer and a rotating polarizer during measurement of a sample, the above-described calibration method of the invention (whose coarse approximation step is described with reference to equations (10)–(15)) is slightly modified in a manner that will be apparent to those of ordinary skill in the art so that the method determines coarse (and then refined) approximations of values $P_0$ and $A_0$ by processing reflectivity data measured at only a single frequency (or frequency range) of incident radiation (rather than tan$\psi$ and cos$\Delta$ spectra comprising reflectivity data measured at each of distinguishable multiple frequencies of incident radiation). Processor 101' of FIG. 12 is programmed to implement this slightly modified version of the above-described calibration method of the invention. Processor 101' can comprise hardware identical to that of processor 101 (of FIG. 4). However, processor 101' but is programmed in a slightly different manner than is processor 101, so that processor 101' processes data (from detector 73) corresponding to a subset of the data processed by processor 101, with processor 101' processing this reduced set of data in the same manner that processor 101 processes data from only one detector of array 173.

Other embodiments of the inventive apparatus comprise not only an ellipsometer, but a spectrophotometer integrated together with an ellipsometer (preferably any of the above-described spectroscopic ellipsometers) as a single instrument. An example of such a spectrophotometer integrated with a spectroscopic ellipsometer is the system described with reference to FIG. 14 of above-referenced U.S. Ser. No. 08/375,353 (modified only by addition of a processor 101 identical to that of FIG. 4 of the present disclosure, programmed for receiving and processing data output from its detectors and for generating control signals for controlling the polarizer, analyzer, and other components thereof to implement the inventive calibration method).

Several embodiments of methods and optical systems according to the present invention have been described. The description is illustrative and not restrictive. Many other variations on the invention will become apparent to those of skill in the art upon review of this disclosure. Merely by way of example, the sample measured by the invention need not be a wafer (it can be any other reflective object), and fold mirrors can be removed where space allows and additional fold mirrors provided where space is limited. The scope of the invention should be determined not merely with reference to the above description, but should be determined with reference to the appended claims along with their full scope of equivalents.

What is claimed is:

1. A method for calibrating an ellipsometer which measures reflectivity data in an operating mode, where the ellipsometer has a polarizer and an analyzer, one of the polarizer and the analyzer is a rotatable element which rotates during the operating mode, and another of the polarizer and the analyzer is a fixed element which remains in a fixed orientation during the operating mode, said method including the steps of:

(a) processing a first set of reflectivity data measured by operating the ellipsometer to generate first data coarsely approximating a first parameter and second data coarsely approximating a second parameter, where the first parameter indicates orientation of the rotatable element at an initial time, and the second parameter indicates offset between the fixed orientation of the fixed element and a corresponding nominal orientation of the fixed element; and (b) processing the first data, the second data, and a second set of reflectivity data measured by operating the ellipsometer, to generate third data indicative of a refined approximation of the first parameter and fourth data indicative of a refined approximation of the second parameter.

2. The method of claim 1, wherein step (b) includes the steps of:

measuring the second set of reflectivity data by operating the ellipsometer at a sequence of different fixed orientations of the fixed element;

processing the second set of reflectivity data to determine sample reflectivity values for each of the fixed orientations; and performing regression, on the first parameter and the second parameter, on the sample reflectivity values.

3. The method of claim 1, wherein the rotatable element is the polarizer, the polarizer rotates with substantially constant speed during measurement of the first set of reflectivity data and the second set of reflectivity data, the second set of reflectivity data includes at least two subsets of data, each of the subsets consists of data measured at a different fixed orientation angle of the analyzer, and step (b) includes the steps of:

processing each of the subsets, with the first data and the second data, to determine sample reflectivity values; and performing regression on the first parameter and the second parameter to generate revised sample reflectivity values, until differences between the revised sample reflectivity values for pairs of the subsets are minimized, wherein those values of the first parameter and the second parameter which result in minimization of said differences are identified as said third data and said fourth data.

4. The method of claim 3, wherein the sample reflectivity values for each of the subsets comprise a $\tan\psi$ value and $\Delta$ is value where $\tan\psi$ is the amplitude of the complex ratio of the p and s components of the reflectivity values and $\cos\Delta$ is the phase of the complex ratio of the reflectivity values.

5. The method of claim 3, wherein the ellipsometer is a spectroscopic ellipsometer, and the sample reflectivity values for each of the subsets comprise a $\tan\psi$ spectrum and $\Delta$ is spectrum where $\tan\psi$ is the amplitude of the complex ratio of the p and s components of the reflectivity values and $\cos\Delta$ is the phase of the complex ratio of the reflectivity values.

6. The method of claim 3, wherein step (a) includes the steps of:

operating the ellipsometer with the analyzer at a first nominal analyzer angle $A_1$ to measure reflectivity data, and processing said reflectivity data to determine a first nominal residual value $R'(A_1)$;

operating the ellipsometer to measure additional reflectivity data with the analyzer at several nominal analyzer angles $A_i$, all approximately equal to $-A_1$, and processing the additional reflectivity data to determine nominal residual values $R'(A_i)$;

identifying a second nominal analyzer angle $A_2$, where $-A_2$ is one of the nominal analyzer angles $A_i$ at which nominal residual value $R'(-A_2)$ is closest to the first nominal residual value; and generating said second data by averaging the first nominal analyzer angle and the second nominal analyzer angle.

7. The method of claim 6, wherein the step of processing the reflectivity data to determine the first nominal residual value $R'(A_1)$ includes the steps of:

processing the reflectivity data to determine fifth data indicative of a $\tan\psi$ value and $\Delta$ is value where $\tan\psi$ is the amplitude of the complex ratio of the p and s component of the reflectivity values and $\cos\Delta$ is the phase of the complex ratio of the reflectivity values; and processing sixth data indicative of the first nominal analyzer angle $A_1$, and the fifth data, to generate data indicative of $$R'(A_1)=(4-\cos^2\Delta)\tan^2\psi\tan^2(A_1)/[\tan^2\psi+\tan^2(A_1)]^2.$$

8. The method of claim 1, wherein the rotatable element is the analyzer, the analyzer rotates with substantially constant speed during measurement of the first set of reflectivity data and the second set of reflectivity data, the second set of reflectivity data includes at least two subsets of data, each of the subsets consists of data measured at a different fixed orientation angle of the polarizer, and step (b) includes the steps of:

processing each of the subsets, with the first data and the second data, to determine sample reflectivity values; and performing regression on the first parameter and the second parameter to generate revised sample reflectivity values, until differences between the revised sample reflectivity values for pairs of the subsets are minimized, whereby those values of the first parameter and the second parameter which result in minimization of said differences are identified as said third data and said fourth data.

9. The method of claim 8, wherein the sample reflectivity values for each of the subsets comprise a $\tan\psi$ value and $\Delta$ is value where $\tan\psi$ is the amplitude of the complex ratio of the p and s components of the reflectivity values and $\cos\Delta$ is the phase of the complex ratio of the reflectivity values.

10. The method of claim 8, wherein the ellipsometer is a spectroscopic ellipsometer, and the sample reflectivity values for each of the subsets comprise a $\tan\psi$ spectrum and $\Delta$ is spectrum where $\tan\psi$ is the amplitude of the complex ratio of the p and s components of the reflectivity values and $\cos\Delta$ is the phase of the complex ratio of the reflectivity values.

11. The method of claim 8, wherein step (a) includes the steps of:

operating the ellipsometer with the polarizer at a first nominal polarizer angle $P'_1$ to measure reflectivity data, and processing said reflectivity data to determine a first nominal residual value $R'(P'_1)$;

operating the ellipsometer to measure additional reflectivity data with the polarizer at several nominal polarizer angles $P'_i$, all approximately equal to $-P'_1$, and processing the additional reflectivity data to determine nominal residual values $R'(P'_i)$;

identifying a second nominal polarizer angle $P'_2$, where $-P'_2$ is one of the nominal polarizer angles $P'_i$ at which nominal residual value $R'(-P'_2)$ is closest to the first nominal residual value; and generating said second data by averaging the first nominal polarizer angle and the second nominal polarizer angle.

12. An ellipsometer, including:

a polarizer and an analyzer, where one of the polarizer and the analyzer is a rotatable element which rotates during an operating mode of the ellipsometer, and another of the polarizer and the analyzer is a fixed element which remains in a fixed orientation during the operating mode;

a processing means; and a detector means for measuring reflectivity data during the operating mode and supplying said reflectivity data to the processing means, where the reflectivity data are indicative of at least one characteristic of radiation that has propagated through the polarizer and the analyzer during the operating mode, wherein the processing means is programmed with software for:

processing a first set of the reflectivity data received from the detector means to generate first data coarsely approximating a first parameter and second data coarsely approximating a second parameter, where the first parameter indicates orientation of the rotatable element at an initial time, and the second parameter indicates offset between the fixed orientation of the fixed element and a corresponding nominal orientation of the fixed element; and processing the first data, the second data, and a second set of the reflectivity data received from the detector means, to generate third data indicative of a refined approximation of the first parameter and fourth data indicative of a refined approximation of the second parameter.

13. The ellipsometer of claim 12, wherein the processing means is programmed with software for:

generating control signals for causing the detector means to measure the second set of reflectivity data during operation of the ellipsometer at a sequence of different fixed orientations of the fixed element;

processing the second set of reflectivity data to determine sample reflectivity values for each of the fixed orientations; and performing regression, on the first parameter and the second parameter, on the sample reflectivity values.

14. The ellipsometer of claim 12, wherein the rotatable element is the polarizer, the polarizer rotates with substantially constant speed during measurement of the first set of reflectivity data and the second set of reflectivity data, and the processing means is programmed with software for:

generating control signals for causing the detector means to measure the second set of reflectivity data during operation of the ellipsometer with a sequence of different fixed orientation angles of the analyzer, so that the second set of reflectivity data includes at least two subsets of data, each of the subsets consisting of data measured at a different fixed orientation angle of the analyzer;

processing each of the subsets, with the first data and the second data, to determine sample reflectivity values; and performing regression on the first parameter and the second parameter to generate revised sample reflectivity values, until an error term for the revised sample reflectivity values for pairs of the subsets is minimized, wherein the processing means identifies those values of the first parameter and the second parameter which result in minimization of said error term as said third data and said fourth data.

15. The ellipsometer of claim 12, wherein the rotatable element is the analyzer, the analyzer rotates with substantially constant speed during measurement of the first set of reflectivity data and the second set of reflectivity data, and the processing means is programmed with software for:

generating control signals for causing the detector means to measure the second set of reflectivity data during operation of the ellipsometer with a sequence of different fixed orientation angles of the polarizer, so that the second set of reflectivity data includes at least two subsets of data, each of the subsets consisting of data measured at a different fixed orientation angle of the polarizer;

processing each of the subsets, with the first data and the second data, to determine sample reflectivity values; and performing regression on the first parameter and the second parameter to generate revised sample reflectivity values, until an error term for the revised sample reflectivity values for pairs of the subsets is minimized, wherein the processing means identifies those values of the first parameter and the second parameter which result in minimization of said error term as said third data and said fourth data.

16. The ellipsometer of claim 12, wherein the ellipsometer is a spectroscopic ellipsometer, the detector means includes an array of detectors, and each of the detectors measures a different subset of the reflectivity data, each said subset consisting of data indicative of a characteristic of radiation in a different frequency range.

17. An ellipsometer for measuring a sample, including:

a source which emits radiation;

a polarizer for polarizing the radiation, thereby producing a sample beam;

an analyzer positioned for receiving radiation of the sample beam that has reflected from the sample, where the analyzer produces an output beam in response to said radiation, one of the polarizer and the analyzer is a rotatable element which rotates during an operating mode of the ellipsometer, and another of the polarizer and the analyzer is a fixed element which remains in a fixed orientation during the operating mode;

detector means for detecting the output beam and generating reflectivity data in response to the output beam; and processing means which receives the reflectivity data from the detector means, where the processing means is programmed with software for automatically performing a calibration operation, and the calibration operation includes the steps of:

processing a first set of the reflectivity data to generate first data coarsely approximating a first parameter and second data coarsely approximating a second parameter, where the first parameter indicates orientation of the rotatable element at an initial time, and the second parameter indicates offset between the fixed orientation of the fixed element and a corresponding nominal orientation of the fixed element; and processing the first data, the second data, and a second set of the reflectivity data, to generate third data indicative of a refined approximation of the first parameter and fourth data indicative of a refined approximation of the second parameter.

18. The ellipsometer of claim 17, wherein the source is a broadband source which emits broadband radiation, the detector means is a spectrometer, and the spectrometer includes photosensitive means for generating reflectivity data indicative of intensity of said output beam at each of a number of different wavelength ranges.

19. The ellipsometer of claim 17, wherein the polarizer is rotatably mounted for rotation about the optical path, the polarizer rotates with substantially constant speed during measurement of the first set of reflectivity data and the second set of reflectivity data, and the processing means is programmed with software for:

generating control signal for causing the detector means to measure the second set of reflectivity data during operation of the ellipsometer with a sequence of different fixed orientation angles of the analyzer, so that the second set of reflectivity data includes at least two subsets of data, each of the subsets consisting of data measured at a different fixed orientation angle of the analyzer;

processing each of the subsets, with the first data and the second data, to determine sample reflectivity values; and performing regression on the first parameter and the second parameter to generate revised sample reflectivity values, until an error term for the revised sample reflectivity values for pairs of the subsets is minimized, whereby the processing means identifies those values of the first parameter and the second parameter which result in minimization of said error term as said third data and said fourth data.

20. The ellipsometer of claim 17, wherein the analyzer is rotatably mounted for rotation about the optical path, the analyzer rotates with substantially constant speed during measurement of the first set of reflectivity data and the second set of reflectivity data, and the processing means is programmed with software for:

generating control signals for causing the detector means to measure the second set of reflectivity data during operation of the ellipsometer with a sequence of different fixed orientation angles of the polarizer, so that the second set of reflectivity data includes at least two subsets of data, each of the subsets consisting of data measured at a different fixed orientation angle of the polarizer;

processing each of the subsets, with the first data and the second data, to determine sample reflectivity values; and performing regression on the first parameter and the second parameter to generate revised sample reflectivity values, until an error term for the revised sample reflectivity values for pairs of the subsets is minimized, whereby those values of the first parameter and the second parameter which result in minimization of said error term are identified as said third data and said fourth data.

* * * * *